(12) United States Patent
Srivastava et al.

(10) Patent No.: US 11,957,912 B2
(45) Date of Patent: Apr. 16, 2024

(54) SENSOR-BASED PAIN MANAGEMENT SYSTEMS AND METHODS

(71) Applicant: Boston Scientific Neuromodulation Corporation, Valencia, CA (US)

(72) Inventors: Kyle Harish Srivastava, Saint Paul, MN (US); Pramodsingh Hirasingh Thakur, Woodbury, MN (US); Dat Thanh Huynh, West Hollywood, CA (US); Bryan Allen Clark, Forest Lake, MN (US); Jianwen Gu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 17/884,794

(22) Filed: Aug. 10, 2022

(65) Prior Publication Data
US 2022/0379119 A1    Dec. 1, 2022

Related U.S. Application Data

(63) Continuation of application No. 17/095,642, filed on Nov. 11, 2020, now Pat. No. 11,439,827, which is a
(Continued)

(51) Int. Cl.
*A61N 1/36* (2006.01)
*A61B 5/00* (2006.01)
(Continued)

(52) U.S. Cl.
CPC ........ *A61N 1/36139* (2013.01); *A61B 5/1118* (2013.01); *A61B 5/6801* (2013.01);
(Continued)

(58) Field of Classification Search
CPC ............ A61N 1/36139; A61N 1/36071; A61B 5/1118; A61B 5/6801
See application file for complete search history.

(56) References Cited

U.S. PATENT DOCUMENTS

| | | | |
|---|---|---|---|
| 4,297,685 A | 10/1981 | Brainard, II | |
| 5,187,675 A | 2/1993 | Dent et al. | |

(Continued)

FOREIGN PATENT DOCUMENTS

| | | | |
|---|---|---|---|
| AU | 2017335497 B2 | 4/2020 | |
| AU | 2017334841 B2 | 7/2020 | |

(Continued)

OTHER PUBLICATIONS

"2015 Sleep in America® Poll Sleep and Pain—Summary of Findings", National Sleep Foundation, (2015), 1-54.
(Continued)

*Primary Examiner* — Catherine M Voorhees
(74) *Attorney, Agent, or Firm* — Schwegman Lundberg & Woessner, P.A.

(57) ABSTRACT

This document discusses, among other things, systems and methods for managing pain of a subject. A system includes a first sensor circuit to sense a first signal indicative of a functional state of the subject, a second sensor circuit to sense a second signal different from the first signal, and a controller circuit. The controller circuit may determine an operating mode of the second sensor circuit according to the sensed first signal, trigger the second senor circuit to sense the second signal under the determined operating mode, and generate a pain score using at least the second signal sensed under the determined operating mode. The pain score may be output to a patient or used for closed-loop control of a pain therapy.

20 Claims, 6 Drawing Sheets

Related U.S. Application Data continuation of application No. 16/034,304, filed on Jul. 12, 2018, now Pat. No. 10,898,718.

(60) Provisional application No. 62/533,789, filed on Jul. 18, 2017.

(51) Int. Cl.
  *A61B 5/11* (2006.01)
  *A61B 5/01* (2006.01)
  *A61B 5/02* (2006.01)
  *A61B 5/021* (2006.01)
  *A61B 5/024* (2006.01)
  *A61B 5/0533* (2021.01)
  *A61B 5/08* (2006.01)
  *A61B 5/318* (2021.01)
  *A61B 5/369* (2021.01)
  *A61B 5/389* (2021.01)
  *A61N 1/05* (2006.01)

(52) U.S. Cl.
  CPC ............ *A61N 1/36071* (2013.01); *A61B 5/01* (2013.01); *A61B 5/02028* (2013.01); *A61B 5/021* (2013.01); *A61B 5/024* (2013.01); *A61B 5/02416* (2013.01); *A61B 5/0533* (2013.01); *A61B 5/0816* (2013.01); *A61B 5/1112* (2013.01); *A61B 5/1116* (2013.01); *A61B 5/112* (2013.01); *A61B 5/1121* (2013.01); *A61B 5/318* (2021.01); *A61B 5/369* (2021.01); *A61B 5/389* (2021.01); *A61B 5/4806* (2013.01); *A61B 5/4824* (2013.01); *A61B 2562/0219* (2013.01); *A61B 2562/0223* (2013.01); *A61B 2562/0261* (2013.01); *A61N 1/0529* (2013.01); *A61N 1/0551* (2013.01); *A61N 1/36053* (2013.01); *A61N 1/36057* (2013.01); *A61N 1/36062* (2017.08)

(56) References Cited

U.S. PATENT DOCUMENTS

| | | | |
|---|---|---|---|
| 5,774,591 A | 6/1998 | Black et al. | |
| 6,016,103 A | 1/2000 | Leavitt | |
| 6,076,011 A | 6/2000 | Hoover | |
| 6,088,040 A | 7/2000 | Oda et al. | |
| 6,173,260 B1 | 1/2001 | Slaney | |
| 6,480,734 B1 | 11/2002 | Zhang et al. | |
| 6,497,658 B2 | 12/2002 | Roizen et al. | |
| 6,654,632 B2 | 11/2003 | Lange et al. | |
| 6,659,968 B1 | 12/2003 | McClure | |
| 6,731,984 B2 | 5/2004 | Cho et al. | |
| 6,871,099 B1 | 3/2005 | Whitehurst et al. | |
| 7,001,337 B2 | 2/2006 | Dekker | |
| 7,004,907 B2 | 2/2006 | Banet et al. | |
| 7,177,686 B1 | 2/2007 | Turcott | |
| 7,189,204 B2 | 3/2007 | Ni et al. | |
| 7,222,075 B2 | 5/2007 | Petrushin | |
| 7,299,086 B2 | 11/2007 | McCabe et al. | |
| 7,376,457 B2 | 5/2008 | Ross | |
| 7,407,485 B2 | 8/2008 | Huiku | |
| 7,463,927 B1 | 12/2008 | Chaouat | |
| 7,566,308 B2 | 7/2009 | Stahmann | |
| 7,627,475 B2 | 12/2009 | Petrushin | |
| 7,636,602 B2 | 12/2009 | Baru Fassio et al. | |
| 7,650,184 B2 | 1/2010 | Walter | |
| 7,678,061 B2 | 3/2010 | Lee et al. | |
| 7,775,993 B2 | 8/2010 | Heruth et al. | |
| 7,957,809 B2 | 6/2011 | Bourget et al. | |
| 7,986,991 B2 | 7/2011 | Prichep | |
| 8,019,439 B2 | 9/2011 | Kuzma et al. | |
| 8,055,348 B2 | 11/2011 | Heruth et al. | |
| 8,083,682 B2 | 12/2011 | Dalal et al. | |
| 8,192,376 B2 | 6/2012 | Lovett et al. | |
| 8,209,182 B2 | 6/2012 | Narayanan | |
| 8,290,596 B2 | 10/2012 | Wei et al. | |
| 8,332,038 B2 | 12/2012 | Heruth et al. | |
| 8,398,556 B2 | 3/2013 | Sethi et al. | |
| 8,447,401 B2 | 5/2013 | Miesel et al. | |
| 8,475,370 B2 | 7/2013 | McCombie et al. | |
| 8,529,459 B2 | 9/2013 | Malker et al. | |
| 8,606,356 B2 | 12/2013 | Lee et al. | |
| 8,688,221 B2 | 4/2014 | Miesel | |
| 8,744,587 B2 | 6/2014 | Miesel et al. | |
| 8,805,518 B2 | 8/2014 | King et al. | |
| 9,066,659 B2 | 6/2015 | Thakur et al. | |
| 9,072,870 B2 | 7/2015 | Wu et al. | |
| 9,119,965 B2 | 9/2015 | Xi et al. | |
| 9,314,168 B2 | 4/2016 | Watson et al. | |
| 9,395,792 B1 | 7/2016 | Kahn et al. | |
| 10,349,212 B2 | 7/2019 | Tartz et al. | |
| 10,610,688 B2 | 4/2020 | Thakur et al. | |
| 10,631,776 B2 | 4/2020 | Annoni et al. | |
| 10,631,777 B2 | 4/2020 | Clark et al. | |
| 10,667,747 B2 | 6/2020 | Annoni et al. | |
| 10,675,469 B2 | 6/2020 | Annoni et al. | |
| 10,729,905 B2 | 8/2020 | Annoni et al. | |
| 10,750,994 B2 | 8/2020 | Annoni et al. | |
| 10,898,718 B2 * | 1/2021 | Srivastava | ......... A61N 1/36139 |
| 10,926,091 B2 | 2/2021 | Srivastava et al. | |
| 10,960,210 B2 | 3/2021 | Srivastava et al. | |
| 11,089,997 B2 | 8/2021 | Annoni et al. | |
| 11,337,646 B2 | 5/2022 | Annoni et al. | |
| 11,395,625 B2 | 7/2022 | Clark et al. | |
| 11,439,827 B2 * | 9/2022 | Srivastava | ............ A61B 5/1118 |
| 11,751,804 B2 | 9/2023 | Annoni et al. | |
| 2001/0037222 A1 | 11/2001 | Platt et al. | |
| 2002/0042563 A1 | 4/2002 | Becerra et al. | |
| 2004/0015091 A1 | 1/2004 | Greenwald et al. | |
| 2005/0010262 A1 | 1/2005 | Sharan et al. | |
| 2005/0209643 A1 | 9/2005 | Heruth et al. | |
| 2007/0167859 A1 | 7/2007 | Finneran et al. | |
| 2007/0213783 A1 | 9/2007 | Pless | |
| 2007/0260285 A1 | 11/2007 | Libbus et al. | |
| 2008/0015659 A1 | 1/2008 | Zhang et al. | |
| 2008/0077192 A1 | 3/2008 | Harry et al. | |
| 2008/0177191 A1 | 7/2008 | Patangay et al. | |
| 2008/0249430 A1 | 10/2008 | John et al. | |
| 2009/0124863 A1 | 5/2009 | Liu et al. | |
| 2009/0192556 A1 | 7/2009 | Wu et al. | |
| 2009/0312663 A1 | 12/2009 | John et al. | |
| 2009/0318986 A1 | 12/2009 | Alo et al. | |
| 2010/0016913 A1 | 1/2010 | Arcot-Krishnamurthy et al. | |
| 2010/0105997 A1 | 4/2010 | Ecker et al. | |
| 2010/0191311 A1 | 7/2010 | Scheiner et al. | |
| 2010/0286549 A1 | 11/2010 | John et al. | |
| 2011/0015702 A1 | 1/2011 | Ternes et al. | |
| 2011/0021928 A1 | 1/2011 | Giovangrandi et al. | |
| 2011/0034760 A1 | 2/2011 | Brynelsen et al. | |
| 2011/0112420 A1 | 5/2011 | Nagata et al. | |
| 2011/0124979 A1 | 5/2011 | Heneghan et al. | |
| 2011/0137134 A1 | 6/2011 | Hemmerling et al. | |
| 2011/0172562 A1 | 7/2011 | Sahasrabudhe et al. | |
| 2011/0224749 A1 | 9/2011 | Ben-David et al. | |
| 2011/0306846 A1 | 12/2011 | Osorio | |
| 2012/0046715 A1 | 2/2012 | Moffitt et al. | |
| 2012/0109012 A1 | 5/2012 | Cinbis | |
| 2012/0150545 A1 | 6/2012 | Simon | |
| 2012/0277818 A1 | 11/2012 | Stancer et al. | |
| 2013/0066394 A1 | 3/2013 | Saab | |
| 2013/0165994 A1 | 6/2013 | Ternes et al. | |
| 2013/0211291 A1 | 8/2013 | Tran | |
| 2013/0268016 A1 | 10/2013 | Xi et al. | |
| 2014/0276188 A1 | 9/2014 | Jardin | |
| 2014/0276549 A1 * | 9/2014 | Osorio | ................... A61B 5/165 604/503 |
| 2014/0277240 A1 * | 9/2014 | Maskara | ............ A61N 1/36571 607/18 |
| 2015/0005842 A1 | 1/2015 | Lee et al. | |
| 2015/0025335 A1 | 1/2015 | Jain et al. | |
| 2015/0148878 A1 | 5/2015 | Yoo et al. | |
| 2015/0289803 A1 | 10/2015 | Wu et al. | |

(56) References Cited

U.S. PATENT DOCUMENTS

| | | | |
|---|---|---|---|
| 2016/0022203 A1 | 1/2016 | Arnold et al. | |
| 2016/0082265 A1 | 3/2016 | Moffitt et al. | |
| 2016/0129272 A1 | 5/2016 | Hou et al. | |
| 2016/0144194 A1 | 5/2016 | Roothans et al. | |
| 2016/0158551 A1 | 6/2016 | Kent et al. | |
| 2016/0192890 A1* | 7/2016 | Averina | A61B 5/0826 600/300 |
| 2016/0198996 A1 | 7/2016 | Dullen | |
| 2016/0243359 A1 | 8/2016 | Sharma | |
| 2016/0302720 A1 | 10/2016 | John et al. | |
| 2016/0350509 A1 | 12/2016 | Sharma | |
| 2016/0361515 A1 | 12/2016 | Jung et al. | |
| 2016/0374567 A1 | 12/2016 | Breslow et al. | |
| 2017/0128722 A1 | 5/2017 | Perez | |
| 2017/0136264 A1 | 5/2017 | Hyde et al. | |
| 2017/0164876 A1 | 6/2017 | Hyde et al. | |
| 2017/0165485 A1 | 6/2017 | Sullivan et al. | |
| 2017/0231568 A1* | 8/2017 | An | A61B 5/02028 600/301 |
| 2018/0078768 A1 | 3/2018 | Thakur et al. | |
| 2018/0085055 A1 | 3/2018 | Annoni et al. | |
| 2018/0085584 A1 | 3/2018 | Thakur et al. | |
| 2018/0110464 A1 | 4/2018 | Annoni et al. | |
| 2018/0126169 A1 | 5/2018 | Hou et al. | |
| 2018/0192941 A1 | 7/2018 | Annoni et al. | |
| 2018/0192942 A1 | 7/2018 | Clark et al. | |
| 2018/0192943 A1 | 7/2018 | Annoni et al. | |
| 2018/0193644 A1 | 7/2018 | Annoni et al. | |
| 2018/0193650 A1 | 7/2018 | Srivastava et al. | |
| 2018/0193651 A1 | 7/2018 | Annoni et al. | |
| 2018/0193652 A1 | 7/2018 | Srivastava et al. | |
| 2018/0229040 A1 | 8/2018 | Srivastava et al. | |
| 2019/0022397 A1 | 1/2019 | Srivastava et al. | |
| 2020/0188673 A1 | 6/2020 | Thakur et al. | |
| 2020/0214623 A1 | 7/2020 | Annoni et al. | |
| 2020/0214624 A1 | 7/2020 | Clark et al. | |
| 2020/0238087 A1 | 7/2020 | Annoni et al. | |
| 2020/0359960 A1 | 11/2020 | Annoni et al. | |
| 2021/0060343 A1 | 3/2021 | Srivastava et al. | |
| 2021/0128921 A1 | 5/2021 | Srivastava et al. | |
| 2021/0178164 A1 | 6/2021 | Srivastava et al. | |
| 2021/0345950 A1 | 11/2021 | Annoni et al. | |

FOREIGN PATENT DOCUMENTS

| | | |
|---|---|---|
| AU | 2018304079 B2 | 12/2020 |
| EP | 1059064 A2 | 12/2000 |
| EP | 1897586 A1 | 3/2008 |
| EP | 3519037 B1 | 7/2020 |
| EP | 3568069 B1 | 4/2021 |
| EP | 3518736 B1 | 8/2021 |
| KR | 20050053824 A | 6/2005 |
| KR | 1020050053824 A | 6/2005 |
| RU | 2559783 C1 | 8/2015 |
| WO | WO-2007007058 A1 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2014151860 A1 | 9/2014 |
| WO | WO-2015060888 A1 | 4/2015 |
| WO | WO-2015128567 | 9/2015 |
| WO | WO-2016025989 A1 | 2/2016 |
| WO | WO-2016077786 A1 | 5/2016 |
| WO | WO-2018052695 A1 | 3/2018 |
| WO | WO-2018063637 A1 | 4/2018 |
| WO | WO-2018063912 A1 | 4/2018 |
| WO | WO-2018080887 A1 | 5/2018 |
| WO | WO-2019018206 A1 | 1/2019 |

OTHER PUBLICATIONS

"U.S. Appl. No. 15/687,925, Final Office Action dated Feb. 14, 2019", 10 pgs.

"U.S. Appl. No. 15/687,925, Non Final Office Action dated Jun. 11, 2019", 11 pgs.

"U.S. Appl. No. 15/687,925, Non Final Office Action dated Oct. 9, 2018", 9 pgs.

"U.S. Appl. No. 15/687,925, Response filed Jan. 9, 2019 to Non Final Office Action dated Oct. 9, 2018", 9 pgs.

"U.S. Appl. No. 15/687,925, Response filed May 13, 2019 to Final Office Action dated Feb. 14, 2019", 11 pgs.

"U.S. Appl. No. 15/688,676, Examiner Interview Summary dated Sep. 25, 2019", 3 pgs.

"U.S. Appl. No. 15/688,676, Final Office Action dated Jul. 29, 2019", 7 pgs.

"U.S. Appl. No. 15/688,676, Non Final Office Action dated Jan. 11, 2019", 7 pgs.

"U.S. Appl. No. 15/688,676, Non Final Office Action dated Oct. 30, 2019", 6 pgs.

"U.S. Appl. No. 15/688,676, Notice of Allowance dated Apr. 14, 2020", 7 pgs.

"U.S. Appl. No. 15/688,676, Response filed Jan. 7, 2020 to Non Final Office Action ated Oct. 30, 2019", 10 pgs.

"U.S. Appl. No. 15/688,676, Response filed Sep. 25, 2019 to Final Office Action dated Jul. 29, 2019", 10 pgs.

"U.S. Appl. No. 15/688,676, Response filed Apr. 9, 2019 to Non Final Office Action dated Jan. 11, 2019", 12 pgs.

"U.S. Appl. No. 15/711,578, Examiner Interview Summary dated Aug. 28, 2019", 3 pgs.

"U.S. Appl. No. 15/711,578, Non Final Office Action dated May 23, 2019", 6 pgs.

"U.S. Appl. No. 15/711,578, Notice of Allowance dated Nov. 25, 2019", 7 pgs.

"U.S. Appl. No. 15/711,578, Response filed Aug. 23, 2019 to Non Final Office Action dated May 23, 2019", 11 pgs.

"U.S. Appl. No. 15/711,578, Supplemental Response filed Aug. 28, 2019 to Non Final Office Action dated May 23, 2019", 11 pgs.

"U.S. Appl. No. 15/788,403, 312 Amendment filed Apr. 22, 2020", 8 pgs.

"U.S. Appl. No. 15/788,403, Corrected Notice of Allowability dated Mar. 18, 2020", 2 pgs.

"U.S. Appl. No. 15/788,403, Non Final Office Action dated Jul. 23, 2019", 9 pgs.

"U.S. Appl. No. 15/788,403, Notice of Allowance dated Jan. 23, 2020", 7 pgs.

"U.S. Appl. No. 15/788,403, PTO Response to Rule 312 Communication dated Apr. 30, 2020", 2 pgs.

"U.S. Appl. No. 15/788,403, Response filed Oct. 8, 2019 to Non Final Office Action dated Jul. 23, 2019", 11 pgs.

"U.S. Appl. No. 15/867,756, Examiner Interview Summary dated Aug. 28, 2019", 3 pgs.

"U.S. Appl. No. 15/867,756, Non Final Office Action dated Jul. 1, 2019", 8 pgs.

"U.S. Appl. No. 15/867,756, Notice of Allowance dated Dec. 19, 2019", 7 pgs.

"U.S. Appl. No. 15/867,756, Response filed Aug. 29, 2019 to Non Final Office Action dated Jul. 1, 2019", 11 pgs.

"U.S. Appl. No. 15/867,760, Examiner Interview Summary dated Aug. 28, 2019", 3 pgs.

"U.S. Appl. No. 15/867,760, Non Final Office Action dated Jul. 1, 2019", 8 pgs.

"U.S. Appl. No. 15/867,760, Notice of Allowance dated Dec. 19, 2019", 7 pgs.

"U.S. Appl. No. 15/867,760, Response filed Aug. 29, 2019 to Non-Final Office Action dated Jul. 1, 2019", 11 pgs.

"U.S. Appl. No. 15/867,767, Non Final Office Action dated Dec. 17, 2019", 11 pgs.

"U.S. Appl. No. 15/867,767, Notice of Allowance dated Apr. 6, 2020", 5 pgs.

"U.S. Appl. No. 15/867,767, Response filed Mar. 4, 2020 to Non Final Office Action dated Dec. 17, 2019", 10 pgs.

"U.S. Appl. No. 15/867,772, Final Office Action dated Oct. 22, 2020", 10 pgs.

(56) References Cited

OTHER PUBLICATIONS

"U.S. Appl. No. 15/867,772, Non Final Office Action dated Apr. 2, 2020", 9 pgs.
"U.S. Appl. No. 15/867,772, Response filed Jun. 30, 2020 to Non Final Office Action dated Apr. 2, 2020", 10 pgs.
"U.S. Appl. No. 15/867,789, Non Final Office Action dated Apr. 2, 2020", 10 pgs.
"U.S. Appl. No. 15/867,801, Non Final Office Action dated Sep. 30, 2019", 10 pgs.
"U.S. Appl. No. 15/867,801, Notice of Allowance dated Feb. 5, 2020", 8 pgs.
"U.S. Appl. No. 15/867,801, Response filed Dec. 18, 2019 to Non Final Office Action dated Sep. 30, 2019", 12 pgs.
"U.S. Appl. No. 15/867,873, Non Final Office Action dated Apr. 3, 2020", 11 pgs.
"U.S. Appl. No. 15/867,873, Notice of Allowance dated Oct. 22, 2020", 5 pgs.
"U.S. Appl. No. 15/867,873, Response filed Jun. 30, 2020 to Non Final Office Action dated Apr. 1, 2020", 10 pgs.
"U.S. Appl. No. 15/888,808, Advisory Action dated Feb. 10, 2020", 2 pgs.
"U.S. Appl. No. 15/888,808, Examiner Interview Summary dated Aug. 3, 2020", 3 pgs.
"U.S. Appl. No. 15/888,808, Examiner Interview Summary dated Nov. 21, 2019", 3 pgs.
"U.S. Appl. No. 15/888,808, Final Office Action dated Dec. 16, 2019", 7 pgs.
"U.S. Appl. No. 15/888,808, Non Final Office Action dated Jul. 2, 2020", 11 pgs.
"U.S. Appl. No. 15/888,808, Non Final Office Action dated Sep. 11, 2019", 7 pgs.
"U.S. Appl. No. 15/888,808, Response filed Jan. 31, 2020 to Final Office Action dated Dec. 16, 2019", 11 pgs.
"U.S. Appl. No. 15/888,808, Response filed Mar. 16, 2020 to Advisory Action dated Feb. 10, 2020", 8 pgs.
"U.S. Appl. No. 15/888,808, Response filed Sep. 29, 2020 to Non Final Office Action dated Jul. 2, 2020", 11 pgs.
"U.S. Appl. No. 15/888,808, Response filed Nov. 19, 2019 to Non Final Office Action dated Sep. 11, 2019", 10 pgs.
"U.S. Appl. No. 16/034,304, Examiner Interview Summary dated Sep. 15, 2020", 3 pgs.
"U.S. Appl. No. 16/034,304, Final Office Action dated Jul. 27, 2020", 11 pgs.
"U.S. Appl. No. 16/034,304, Non Final Office Action dated Apr. 3, 2020", 15 pgs.
"U.S. Appl. No. 16/034,304, Notice of Allowance dated Sep. 29, 2020", 8 pgs.
"U.S. Appl. No. 16/034,304, Response filed Jun. 30, 2020 to Non Final Office Action dated Apr. 3, 2020", 13 pgs.
"U.S. Appl. No. 16/034,304, Response filed Sep. 16, 2020 to Final Office Action dated Jul. 27, 2020", 11 pgs.
"U.S. Appl. No. 16/821,161, Non Final Office Action dated Jan. 3, 2022", 5 pgs.
"U.S. Appl. No. 16/821,161, Response filed Jan. 27, 2022 to Non Final Office Action dated Jan. 3, 2022", 8 pgs.
"U.S. Appl. No. 17/095,642, Non Final Office Action dated Feb. 17, 2022", 13 pgs.
"U.S. Appl. No. 17/095,642, Notice of Allowance dated May 4, 2022", 8 pgs.
"U.S. Appl. No. 17/095,642, Response filed Mar. 31, 2022 to Non Final Office Action dated Feb. 17, 2022", 9 pgs.
"Australian Application Serial No. 2017325823, First Examination Report dated Jun. 19, 2019", 3 pgs.
"Australian Application Serial No. 2017334841, First Examination Report dated Jun. 24, 2019", 3 pgs.
"Australian Application Serial No. 2017334841, Response filed Feb. 6, 2020 to First Examination Report dated Jun. 24, 2019", 14 pgs.
"Australian Application Serial No. 2017335497, First Examination Report dated Jun. 26, 2019", 3 pgs.
"Australian Application Serial No. 2017335497, Response filed Nov. 27, 2019 to First Examination Report dated Jun. 26, 2019", 18 pgs.
"Australian Application Serial No. 2018304079, First Examination Report ated Jun. 11, 2020", 5 pgs.
"Australian Application Serial No. 2018304079, Response filed Oct. 29, 2020 to First Examination Report dated Jun. 11, 2020", 14 pgs.
"European Application Serial No. 17762308.9, Response to Communication pursuant to Rules 161 & 162 filed Nov. 26, 2019", 23 pgs.
"European Application Serial No. 17778108.5, Response to Communication Pursuant to Rules 161 and 162 filed Dec. 2, 2019", 3 pgs.
"European Application Serial No. 17794503.7, Response to Communication Pursuant to Rules 161 and 162 filed Dec. 30, 2019", 11 pgs.
"European Application Serial No. 18701908.8, Communication Pursuant to Article 94(3) EPC dated May 20, 2020", 6 pgs.
"European Application Serial No. 18701908.8, Response filed Sep. 29, 2020 to Communication Pursuant to Article 94(3) EPC dated May 20, 2020", 29 pgs.
"European Application Serial No. 18701908.8, Response to Communication Pursuant to Rules 161 and 162 filed Mar. 16, 2020", 8 pgs.
"European Application Serial No. 18702012.8, Response to Communication Pursuant to Rules 161 and 162 filed Mar. 11, 2020", 12 pgs.
"European Application Serial No. 18704105.8, Response to Communication Pursuant to Rules 161 and 162 filed Feb. 27, 2020", 10 pgs.
"European Application Serial No. 21188652.8, Extended European Search Report dated Nov. 24, 2021", 9 pgs.
"European Application Serial No. 21189952.1, Extended European Search Report dated Nov. 22, 2021", 7 pgs.
"International Application Serial No. PCT/US2017/048867, International Preliminary Report on Patentability dated Mar. 28, 2019", 8 pgs.
"International Application Serial No. PCT/US2017/048867, International Search Report dated Nov. 13, 2017", 5 pgs.
"International Application Serial No. PCT/US2017/048867, Written Opinion dated Nov. 13, 2017", 6 pgs.
"International Application Serial No. PCT/US2017/048896, International Preliminary Report on Patentability dated Apr. 11, 2019", 8 pgs.
"International Application Serial No. PCT/US2017/048896, International Search Report dated Nov. 27, 2017", 5 pgs.
"International Application Serial No. PCT/US2017/048896, Written Opinion dated Nov. 27, 2017", 6 pgs.
"International Application Serial No. PCT/US2017/052685, International Preliminary Report on Patentability dated Apr. 11, 2019", 6 pgs.
"International Application Serial No. PCT/US2017/052685, International Search Report dated Jan. 4, 2018", 5 pgs.
"International Application Serial No. PCT/US2017/052685, Written Opinion dated Jan. 4, 2018", 6 pgs.
"International Application Serial No. PCT/US2017/057367, International Preliminary Report on Patentability dated May 9, 2019", 6 pgs.
"International Application Serial No. PCT/US2017/057367, International Search Report dated Jan. 19, 2018", 4 pgs.
"International Application Serial No. PCT/US2017/057367, Written Opinion dated Jan. 19, 2018", 4 pgs.
"International Application Serial No. PCT/US2018/013251, International Preliminary Report on Patentability dated Jul. 25, 2019", 7 pgs.
"International Application Serial No. PCT/US2018/013251, International Search Report dated Apr. 12, 2018", 4 pgs.
"International Application Serial No. PCT/US2018/013251, Written Opinion dated Apr. 12, 2018", 5 pgs.
"International Application Serial No. PCT/US2018/013257, International Preliminary Report on Patentability dated Jul. 25, 2019", 8 pgs.

(56) References Cited

OTHER PUBLICATIONS

"International Application Serial No. PCT/US2018/013257, International Search Report dated Apr. 19, 2018", 4 pgs.
"International Application Serial No. PCT/US2018/013257, Written Opinion dated Apr. 19, 2018", 6 pgs.
"International Application Serial No. PCT/US2018/013268, International Preliminary Report on Patentability dated Jul. 25, 2019", 13 pgs.
"International Application Serial No. PCT/US2018/013268, International Search Report dated Apr. 30, 2018", 5 pgs.
"International Application Serial No. PCT/US2018/013268, Written Opinion dated Apr. 30, 2018", 11 pgs.
"International Application Serial No. PCT/US2018/041860, International Preliminary Report on Patentability dated Jan. 30, 2020", 7 pgs.
"International Application Serial No. PCT/US2018/041860, International Search Report dated Oct. 17, 2018", 4 pgs.
"International Application Serial No. PCT/US2018/041860, Written Opinion dated Oct. 17, 2018", 5 pgs.
Ahern, David K., et al., "Comparison of lumbar paravertebral EMG patterns in chronic low back pain patients and non-patient controls", Pain, 34, (1988), 153-160.
Allum, John H.J., et al., "A speedy solution for balance and gait analysis: angular velocity measured at the centre of body mass", Current Opinion in Neurology 18, (2005), 15-21.
Alo, Kenneth M., et al., "Effect of Spinal Cord Stimulation on Sensory Nerve Conduction Threshold Functional Measures", Neuromodulation, vol. 3, No. 3, (2000), 145-154.
Ambady, Nalini, et al., "Thin Slices of Expressive Behavior as Predictors of Interpersonal Consequences: A Meta-Analysis", Psychological Bulletin, 1992, vol. 111, No. 2, 256-274.
Annoni, Elizabeth M., et al., "Method and Apparatus for Pain Management Using Objective Pain Measure", U.S. Appl. No. 62/400,336, filed Sep. 27, 2016.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Arsenault, Marianne, et al., "Pain Modulation Induced by Respiration: Phase and Frequency Effects", Neuroscience 252, (2013), 501-511.
Artner, Juraj, et al., "Prevalence of sleep deprivation in patients with chronic neck and back pain: a retrospective evaluation of 1016 patients", Journal of Pain Research: 6, (2013), 1-6.
Ashraf, A B, et al., "The painful face—Pain expression recognition using active appearance models", Image and Vision Computing Elsevier Guildford, GB, vol. 27, No. 12, (Nov. 1, 2009), 1788-1796.
Bakker, Jorn, et al., "What's your current stress level? Detection of stress patterns from GSR sensor data", Eindhoven University of Technology—The Netherlands, (2011), 1-8.
Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.
Banos, Oresti, et al., "PhysioDroid: Combining Wearable Health Sensors and Mobile Devices for a Ubiquitous, Continuous, and Personal Monitoring", The Scientific World Journal, vol. 2014 Article ID 190824, (2014), 11 pgs.
Bansevicius, Dalius, et al., "Mental stress of long duration: EMG activity, perceived tension, fatigue, and pain development in pain-free subjects", Headache: The Journal of Head and Face Pain; 37.8, (1997), 499-510.

Barad, Meredith J., et al., "Complex Regional Pain Syndrome Is Associated With Structural Abnormalities in Pain-Related Regions of the Human Brain", The Journal of Pain, vol. 15, No. 2, (Feb. 2014), 197-203.
Barkley, Jacob E., et al., "The effect of spinal cord stimulation unit revision on perceived pain, anxiety, mobility and physical activity in individuals with low back/lower extremity pain", Kent State University - The Spine and Pain Institute, Presented at Annual Meeting of the North American Neuromodulation Society (NANS) on Dec. 11-14, 2014, 1 pg.
Bartlett, Marian Stewart, et al., "Automatic Decoding of Facial Movements Reveals Deceptive Pain Expressions", Current Biology 24, 738-743, Mar. 31, 2014.
Beneck, George J., et al., "Spectral analysis of EMG using intramuscular electrodes reveals non-linear fatigability characteristics in persons with chronic low back pain", Journal of Electromyography and Kinesiology 23, (2013), 70-77.
Ben-Israel, Nir, et al., "Monitoring the nociception level: a multi-parameter approach", J Clin Monit Comput, (Jul. 2012), 10 pgs.
Ben-Israel, Nir, et al., "Monitoring the nociception level: a multi-parameter approach", J Clin Monit Comput 27, (2013), 659-668.
Berthomier, Christian, et al., "Automatic analysis of single-channel sleep EEG: validation in healthy individuals", Sleep—New York Then Westchester—30.11, (2007), 1587-1595.
Boselli, E., et al., "Prediction of immediate postoperative pain using the analgesia/ nociception index: a prospective observational study", British Journal of Anaesthesia 112 (4):, (2014), 715-721.
Boselli, E., et al., "Prospective observational study of the non-invasive assessment of immediate postoperative pain using the analgesia/nociception index (ANI)", British Journal of Anaesthesia 111, (2013), 453-459.
Broucqsault-Dedrie, Celine, et al., "Measurement of Heart Rate Variability to Assess Pain in Sedated Critically Ill Patients: A Prospective Observational Study", PLOS One, (Jan. 25, 2016), 1-11.
Bunde, Armin, et al., "Correlated and uncorrelated regions in heart-rate fluctuations during sleep", Physical Review Letters 85.17, (2000), 3736-3739.
Chan, C. W.Y., et al., "Subjective pain sensation is linearly correlated with the Flexion reflex in man", Brain Research, 479, (1989), 145-150.
Chapman, C. Richard, et al., "Phasic pupil dilation response to noxious stimulation in normal volunteers: relationship to brain evoked potentials and pain report", (1999), 44-52.
Chen, Shuzhen, et al., "The role of the autonomic nervous system in hypertension: a bond graph model study", Physiological measurement 29.4 (2008): 473, (2008), 473-495.
Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013,, (2013), 1-10.
Chuang, Chiung-Cheng, et al., "Photoplethysmography variability as an alternative approach to obtain heart rate variability information in chronic pain patient", J Clin Monit Comput—Published online, (Feb. 24, 2015), 1-6.
Chung, Ok Y., "Baroreflex sensitivity associated hypoalgesia in healthy states is altered by chronic pain", Pain 138, (2008), 87-97.
Ciampi De Andrade, Daniel, et al., "Neurophysiological assessment of spinal cord stimulation in failed back surgery syndrome", Pain 150, (2010), 485-491.
Cinaz, Burcu, et al., "Monitoring of mental workload levels during an everyday life office-work scenario", Pers Ubiquit Comput 17, (2013), 229-239.
Clark, Bryan Allen, et al., "Pain Management Based on Functional Measurements", U.S. Appl. No. 62/445,075, filed Jan. 11, 2017.
Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.
Dansie, Elizabeth J., et al., "Activity in Adults with Chronic Widespread Pain", The Journal of Pain—Accepted Manuscript, (2014), 33 pgs.

(56) References Cited

OTHER PUBLICATIONS

Davydov, Dmitry M., et al., "Cardiovascular activity and chronic pain severity", Physiology & Behavior 152, 203-216 (2015).
De-La-Herran, Alvaro M., et al., "Gait Analysis Methods: An Overview of Wearable and Non-Wearable Systems, Highlighting Clinical Applications", Sensors 14, (2014), 3362-3394.
Denk, Franziska, et al., "Chronic Pain: Emerging Evidence for the Involvement of Epigenetics", Neuron 73 (3), (2012), 435-444.
Duschek, S., "Relationship between baroreceptor cardiac reflex sensitivity and pain experience in normotensive individuals", International Journal of Psychophysiology 65, (2007), 193-200.
Eisenberg, Elon, et al., "Quantitative Sensory Testing for Spinal Cord Stimulation in Patients With Chronic Neuropathic Pain", (2006), 161-165.
Elgendi, Mohamed, "On the analysis of fingertip photoplethysmogram signals", Current cardiology reviews 8.1, (2012), 14-25.
Evans, Subhadr, et al., "Heart rate variability as a biomarker for autonomic nervous system response differences between children with chronic pain and healthy control children", Journal of Pain Research 3.6, (2013), 449-457.
Fagius, J., et al., "The cold pressor test: effects on sympathetic nerve activity in human muscle and skin nerve fascicles", Acta physiologica Scandinavica 137.3, (1989), 325-334.
Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.
Foo, H., et al., "Brainstem modulation of pain during sleep and waking", Sleep medicine reviews 7.2, (2003), 145-154.
Frederiks, Joost, et al., "Within-subject electrocardiogramences at equal heart rates: role of the autonomic nervous system", Pflügers Archiv 441.5, (2001), 717-724.
Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).
Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.
Gesche, Heiko, et al., "Continuous blood pressure measurement by using the pulse transit time: comparison to a cuff-based method", European journal of applied physiology 112.1, (2012), 309-315.
Godfrey, A., et al., "Direct measurement of human movement by accelerometry", Medical Engineering & Physics 30 (2008) 1364-1386.
Godfrey, A., et al., "Instrumenting gait with an accelerometer: a system and algorithm examination", Medical Engineering & Physics, Mar. 2015, doi:10.1016/j.medengphy.2015.02.003, 24 pgs.
Gouveia, S., et al., "Assessing Baroreflex Sensitivity in the Sequences Technique: Local versus Global Approach", Computers in Cardiology, 32, (2005), 279-282.
Granovsky, Yelena, et al., "Objective Correlate of Subjective Pain Perception by Contact Heat-Evoked Potentials", The Journal of Pain, vol. 9, No. 1, (Jan. 2008), 53-63.
Green, Alexande L., "Measurement of muscle sympathetic nerve activity reveals true sympathetic changes in chronic pain", Exp Physiol 97.10, (2012), 1083.
Hallman, David, et al., "Autonomic regulation, physical activity and perceived stress in subjects with musculoskeletal pain: 24-hour ambulatory monitoring", International Journal of Psychophysiology 86, (2012), 276-282.
Hallman, David M., et al., "Changes in physical activity and heart rate variability in chronic neck-shoulder pain: monitoring during work and leisure time", Int Arch Occup Environ Health 87, (2014), 735-744.
Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907482, 11 pages, http://dx.doi.org/10.1155/2015/907482, 11 pages.
Hartwich, Doreen, et al., "Effect of muscle metaboreflex activation on spontaneous cardiac baroreflex sensitivity during exercise in humans", J Physiol 589.24, (2011), 6157-6171.
Jensen, MP, et al., "Brain EEG activity correlates of chronic pain in persons with spinal cord injury: clinical implications", Nature; Spinal Cord; 51, (Jul. 17, 2012), 55-58.
Jess, Gunnar, et al., "Monitoring heart rate variability to assess experimentally induced pain using the analgesia nociception index—A randomised volunteer study", Eur J Anaesthesiol 32, (2015), 1-8.
Kang, Jon-Eun, et al., "Pulse transit time shows vascular changes caused by propofol in children", J Clin Monit Comput 29, (2015), 533-537.
Keefe, Francis J,, et al., "An Objective Approach to Quantifing Pain Behavior and Gait Patterns in Low Back Pain Patients", Pain, 21, (1985), 153-161.
Kemler, Marius A., et al., "Impact of Spinal Cord Stimulation on Sensory Characteristics in Complex Regional Pain Syndrome Type 1—A Randomized Trial", Anesthesiology, 95, (2001), 72-80.
Keshari, Kayvan R., et al., "Lactic Acid and Proteoglycans as Metabolic Markers dor Discogenic Back Pain", SPINE, vol. 13, No. 3, (2008), 312-317.
Kim, Young Uk, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.
Kodituwakku, Sandun, et al., "Point Process Respiratory Sinus Arrhythmia Analysis during Deep Tissue Pain Stimulation", Computing in Cardiology 38, (2011), 193-196.
Koenig, J., et al., "Heart rate variability and experimentally induced pain in healthy adults: A systematic review", European Journal of Pain 18, (2014), 301-314.
Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.
La Rovere, Maria Teresa, et al., "Baroreflex Sensitivity: Measurement and Clinical Implications", Ann Noninvasive Electrodardiol, 13(2):191-207, 2008.
Lamoth, Claudine J.C., et al., "How do persons with chronic low back pain speed up and slow down? Trunk-pelvis coordination and erector spinae activity during gait", Gait & Posture 23, (2006), 230-239.
Lamoth, Claudine J.C., et al., "Pelvis-Thorax Coordination in the Transverse Plane During Walking in Persons With Nonspecific Low Back Pain", SPINE, vol. 27, No. 4, (2002), E92-E99.
Lane, James D., et al., "Respiratory Sinus Arrhythmia and Cardiovascular Responses to Stress", Psychophysiology, vol. 29, No. 4, (1992), 461-470.
Latremoliere, Alban, et al., "Reduction of Neuropathic and Inflammatory Pain through Inhibition of the Tetrahydrobiopterin Pathway", Neuron, 86 (6), (2015), 1393-1406.
Ledowski, Thomas, et al., "The influence of age and sex on the relationship between heart rate variability, haemodynamic variables and subjective measures of acute post-operative pain", European Journal of Anaesthesiology, vol. 28, No. 6, (2011), 433-437.
Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.
Lidberg, Lars, et al., "Sympathetic Skin Nerve Dischai gcs in Relation lo Anipliliule ol Skin Resistance Responses", Psychophysiology, vol. 18, No. 3, (May 1981), 268-270.
Littlewort, Gwen C., et al., "Automatic Coding of Facial Expressions Displayed During Posed and Genuine Pain", Image and Vision Computing, 27(12) p. 1741-1844.
Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Looney, David, et al., "The In-the-Ear Recording Concept", IEEE Pulse Nov./Dec. 2012, 32-42.
Marchi, Antonio, et al., "Pain Biomarkers", Clin Drug Invest, 29 Suppl 1, (2009), 41-46.

(56) References Cited

OTHER PUBLICATIONS

Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C,, et al., "Quantitative sensory testing in the German Research Network on Neuropathic Pain (DFNS): Somatosensory abnormalities in 1236 patients with different neuropathic pain syndromes", Pain 150, (2010), 439-450.
Mcbeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.
Mccarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.
Mccracken, Lance M., et al., "Disrupted sleep patterns and daily functioning in patients with chronic pain", Pain Res Manage vol. 7 No. 2 Summer 2002 75-79.
Mikkelsen, Kaare B., et al., "EEGRecordedfromtheEar:CharacterizingtheEar-EEGMethod", FrontiersinNeuroscience|www.frontiersin.org, Nov. 2015 |vol. 9|Article438, 8 pgs.
Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.
Moseley, G. Lorimer, et al., "Tactile Discrimination, but not tactile stimulation alone, reduces chronic limg pain", Pain 137, (2008), 600-608.
Moxham, I.M., "Understanding Arterial Pressure Waveforms", Southern African Journal of Anaesthesia and Analgesia 9.1, (2003), 40-42.
Mukkamala, R., et al., "Toward ubiquitous blood pressure monitoring via pulse transit time: theory and practice", IEEE Transactions on Biomedical Engineering 62.8, (2015), 1879-1901.
Mylius, Vett, et al., "Sex differences in nociceptive withdrawal reflex and pain perception", Somatosensory and Motor Research 22 (3), (Sep. 2005), 207-211.
Neblett, Randy, et al., "What Is The Best Surface EMG Measure of Lumbar Flexion-Relation for Distinguishing Chronic Low Back Pain Patients From Pain-Free Controls?", Clin J Pain 29 (4)—NIH Public Access, (Apr. 2013), 334-340.
Ng, Joseph, et al., "EMG activity of trunk muscles and torque output during isometric axial rotation exertion: a comparison between back pain patients and matched controls", Journal of Orthopaedic Research; 20, (2002), 112-121.
Palermo, Tonya M., et al., "Subjective Sleep Disturbances in Adolescents With Chronic Pain: Relationship to Daily Functioning and Quality of Life", The Journal of Pain, vol. 6, No. 3, (March 2995), 201-207.
Panjabi, Manohar, "Clinical spinal instability and low back pain", Journal of Electromyography and Kinesiology 13, (2003), 371-379.
Patti, Gary J., et al., "Metabolomics implicates altered sphingolipids in chronic pain of neuropathic origin", nature chemical biology, vol. 8, (Mar. 2012), 232-234.
Perruchoud, Christophe, et al., "Assessment of Physical Activity of Patients with Chronic Pain", Neuromodulation: Technology at the Neural Interface; 17, (2012), 42-47.
Pinheiro, Eulália Silva Dos Santos, et al., "Electroencephalographic Patterns in Chronic Pain: A Systematic Review of the Literature", PLOS ONE | DOI:10.1371/journal.pone.0149085 Feb. 25, 2016, 27 pgs.
Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.
Pleger, Burkhard, et al., "Patterns of cortical reorginization parallel impaired tactile discrimination and pain intensity in complex regional pain syndrome", NeuroImage 32, (2006), 503-510.

Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.
Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.
Prichep, Leslie S., et al., "Evaluation of the Pain Matrix Using EEG Source Localization: A Feasibility Study", Pain Medicine 12, (2011), 1241-1248.
Prkachin, Kenneth, "The consistency of facial expressions of pain: a comparison across modalities", PAIN, 51, (1992), 279-306.
Raminen, Tina, et al., "The Impact of Spinal Cord Stimulation on Sleep Patterns", Neuromodulation 19, (2016), 477-481.
Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.
Rhudy, Jamie L., et al., "Defining the nociceptive flexion reflex (NFR) threshold in human participants: A comparison of different scoring criteria", Pain 128, (2007), 244-253.
Roy, Sourav Dey, et al., "An Approach for Automatic Pain Detection through Facial Expression", Procedia Computer Science 84 (2016) 99-106.
Sacco, Marcella, et al., "The Relationship Between Blood Pressure and Pain", The Journal of Clinical Hypertension vol. 15, No. 8, (Aug. 2013), 600-605.
Sano, Akane, et al., "Quantitative analysis of wrist electrodermal activity during sleep", Int J Psychophysiol. Dec. 2014 ; 94(3), (2014), 382-389.
Sarnthein, Johannes, et al., "Increased EEG power and slowed dominant frequncy in patients with neurogenic pain", Brain 129, (2005), 55-64.
Sato, Karina L/, et al., "Spinal Cord Stimulation (SCS) Improves Decreased Physical Activity Induced by Nerve Injury", Behavioral Neuroscience, vol. 128, No. 5, (2914), 625-632.
Sawada, Yukihiro, et al., "Normalized pulse volume (NPV) derived photo-plethysmography as a more valid measure of the finger vascular tone", International Journal of Psychophysiology 41, (2001), 1-10.
Sayar, Kemal, et al., "Sleep Quality in Chronic Pain Patients", Can J. Psychiatry, vol. 47, No. 9, (Nov. 2002), 844-848.
Schulman, Joshua J., et al., "Thalamocortical dysrhythmia syndrome: MEG imaging of neuropathic pain", (Jul. 25, 2014), 33-39.
Schulz, Enrico, et al., "Prefrontal Gamma Oscillations Encode Tonic Pain in Humans", Cerebral Cortex 2015, (Mar. 8, 2015), 1-8.
Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.
Shouldice, R., "PR and PP ECG intervals as indicators of autonomic nervous innervation of the cardiac sinoatrial and atrioventricular nodes", Neural Engineering, 2003. Conference Proceedings. First International IEEE Embs Conference on. IEEE, (Mar. 2003), 261-264.
Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.
Sihvonen, T., et al., "Electric behavior of low back muscles during lumbar pelvic rhythm in low back pain patients and healthy controls", Archives of physical medicine and rehabilitation; 72.13, (1991), 1080-1087.
Simoes, Mario A., "Feasibility of Wearable Sensors to Determine Gait Parameters", University of South Florida Scholar Commons, (2011), 1-98.
Skljarevski, V., et al., "The nociceptive flexion reflex in humans—review article", Pain, 96, (2002), 3-8.
Smallwood, Rachel F., et al., "Structural Brain Anomalies and Chronic Pain: A Quantitative Meta-Analysis of Gray Matter Volume", The Journal of Pain, vol. 14, No. 7, (Jul. 2013), 663-675.

(56) References Cited

OTHER PUBLICATIONS

Sotocinal, S G, et al., "The Rat Grimace Scale partially automated method for quantifying pain in the laboratory rat via facial expressions", Molecular Pain Biomed Central, London, GB, vol. 7 no. 1, (Jul. 29, 2011), 1744-8069.

Srivastava, Kyle Harish, et al., "Pain Management Based on Cardiovascular Parameters", U.S. Appl. No. 62/445,053, filed Jan. 11, 2017.

Srivastava, Kyle Harish, et al., "Pain Management Based on Emotional Expression Measurements", U.S. Appl. No. 62/445,082, filed Jan. 11, 2017.

Staud, Roland, "Heart rate variability as a biomarker of fibromyalgia syndrome", Fut Rheumatol 3 (5)—NIH Public Access, (Oct. 1, 2008), 475-483.

Storm, H., et al., "Skin conductance correlates with perioperative stress", Acta Anaesthesiol Scand 46, (2002), 887-895.

Sturgeon, John A., et al., "Respiratory Sinus Arrhythmia: a Marker of Resilience to Pain Induction", Int.J. Behav. Med. 21, (2014), 961-965.

Swenne, C. A., "Baroreflex sensitivity: mechanisms and measurement", Neth Heart J 21, (2013), 58-60.

Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.

Tagliazucchi, Enzo, et al., "Brain resting state is disrupted in chronic back pain patients", Neurosci Lett. 485 (1)—NIH Public Access, (Nov. 12, 2010), 26-31.

Tao, Weijun, et al., "Gait Analysis Using Wearable Sensors", Sensors 12, (2012), 2255-2283.

Tauda, Makoto, et al., "P2X4receptorsandneuropathicpain", Frontiers in Cellular Neuroscience, vol. 7, Article 191, (Oct. 28, 2013), 1-6.

Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.

Thakur, Pramodsingh Hirasingh, et al., "Method and Apparatus for Pain Control Using Baroreflex Sensitivity During Posture Change", U.S. Appl. No. 62/412,587, filed Oct. 25, 2016.

Thakur, Pramodsingh Hirasingh, et al., "Systems and Methods for Closed-Loop Pain Management", U.S. Appl. No. 62/400,313, filed Sep. 27, 2016.

Thankur, Pramodsingh Hirasingh, et al., "Method and Apparatus for Pain Management Using Heart Sounds", U.S. Appl. No. 62/395,641, filed Sep. 16, 2016.

Theuvenel, Peter J., et al., "Responses to Median and Tbial Nerve Stimulation in Patients with Chronic Neuropathic Pain", Brain Topography, vol. 11, No. 4, (1999), 306-313.

Uceyler, Nuncan, et al., "Differential expression of cytokines in painful and painless neuropathies", (2007).

Uzar, E., et al., "Serum cytokine and pro-brain natriuretic peptide (BNP) levels in patients with migraine", European Review for Medical and Pharmacological Sciences; 15, (2011), 1111-1116.

Van Velzen, Marit H.N., et al., "Effect of heat-induced pain stimuli on pulse transit time and pulse wave amplitude in healthy volunteers", Physiological Measurement 37, (2016), 52-66.

Villarejo, Viqueira Maria, et al., "A Stress Sensor Based on Galvanic Skin Response (GSR) Controlled by ZigBee", Sensors 12, (2012), 6075-6101.

Walton, K. D., et al., "Abnormal thalamocortical activity in patients with Complex Regional Pain Syndrome (CRPS) Type 1", Pain 150, (2010), 41-51.

Willer, Jean Claude, "Comparative Study of Perceived Pain and Nociceptive Flexion Reflex in Man", Pain, 3, (1977), 69-80.

Williams, Dewayne P., et al., "Effects of Chronic Pelvic Pain on Heart Rate Variability in Women", The Journal of Urology, vol. 194,, (Nov. 2015), 1-6.

Wong, Arnold Y.L., et al., "Does experimental low back pain change posteroanterior lumbar spinal stiffness and trunk muscle activity? A randomized crossover study", Clinical Biomechanics 34, (2016), 45-52.

Wong, Jih-Sen, et al., "A comparative study of pulse rate variability and heart rate variability in healthy subjects", J Clin Monit Comput 26, (2012), 107-114.

Wu, Hao-Yu, et al., "Eulerian Video Magnification for Revealing Subtle Changes in the World", ACM Transactions on Graphics 31(4), (2012), 1-8.

Zamuner, Antonio R., et al., "Respiratory Sinus Arrhythmia and its Association with Pain in Women with Fibromyalgia Syndrome", Pain Practice, vol. 16, Issue 6, (2016), 704-711.

Zamuner, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.

Zeng, Zhihong, et al., "A Survey of Affect Recognition Methods: Audio, Visual and Spontaneous Expressions", ICMI'07, Nov. 12-15, 2007, 126-133.

Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.

Zhou, Jing, et al., "Recurrent Convolutional Neural Network Regression for Continuous Pain Intensity Estimation in Video", arXiv preprint arXiv: 1605.00894 (2016) 84-92.

Zhou, Jing, et al., "Recurrent Convolutional Neural Network Regression for Continuous Pain Intensity Estimation in Video", Technical Report, (May 3, 2016), 1-11.

"U.S. Appl. No. 15/867,772, Advisory Action dated Dec. 22, 2020", 4 pgs.

"U.S. Appl. No. 15/867,772, Examiner Interview Summary dated Apr. 29, 2021", 2 pgs.

"U.S. Appl. No. 15/867,772, Examiner Interview Summary dated Dec. 11, 2020", 2 pgs.

"U.S. Appl. No. 15/867,772, Notice of Allowance dated Apr. 23, 2021", 5 pgs.

"U.S. Appl. No. 15/867,772, Response filed Dec. 15, 2020 to Final Office Action ated Oct. 22, 2020", 12 pgs.

"U.S. Appl. No. 15/888,808, Notice of Allowance dated Nov. 30, 2020", 9 pgs.

"U.S. Appl. No. 16/800,822, Non Final Office Action dated Nov. 29, 2021", 5 pgs.

"U.S. Appl. No. 16/800,822, Notice of Allowance dated May 18, 2022", 7 pgs.

"U.S. Appl. No. 16/800,822, Response filed Feb. 3, 2022 to Non Final Office Action dated Nov. 29, 2021", 7 pgs.

"U.S. Appl. No. 16/820,474, Corrected Notice of Allowability dated Feb. 9, 2022", 2 pgs.

"U.S. Appl. No. 16/820,474, Non Final Office Action dated Oct. 12, 2021", 7 pgs.

"U.S. Appl. No. 16/820,474, Notice of Allowance dated Jan. 25, 2022", 7 pgs.

"U.S. Appl. No. 16/820,474, Response filed Dec. 16, 2021 to Non Final Office Action dated Oct. 12, 2021", 9 pgs.

"U.S. Appl. No. 16/821,161, Notice of Allowance dated Apr. 4, 2022", 7 pgs.

"U.S. Appl. No. 16/848,580, Examiner Interview Summary dated Feb. 4, 2022", 3 pgs.

"U.S. Appl. No. 16/848,580, Examiner Interview Summary dated Jun. 29, 2022", 2 pgs.

"U.S. Appl. No. 16/848,580, Final Office Action dated May 10, 2022", 17 pgs.

"U.S. Appl. No. 16/848,580, Non Final Office Action dated Jan. 4, 2022", 14 pgs.

"U.S. Appl. No. 16/848,580, Response filed Feb. 2, 2022 to Non Final Office Action dated Jan. 4, 2022", 11 pgs.

"U.S. Appl. No. 16/848,580, Response filed Jun. 27, 2022 to Final Office Action dated May 10, 2022", 12 pgs.

"U.S. Appl. No. 16/986,519, Non Final Office Action dated Oct. 5, 2022", 11 pgs.

(56) References Cited

OTHER PUBLICATIONS

"U.S. Appl. No. 16/986,519, Notice of Allowance dated Apr. 24, 2023", 8 pgs.

"U.S. Appl. No. 16/986,519, Response filed Jan. 4, 2023 to Non Final Office Action dated Oct. 5, 2022", 10 pgs.

"European Application Serial No. 18704105.8, Communication Pursuant to Article 94(3) EPC dated Jan. 5, 2022", 9 pgs.

"European Application Serial No. 18704105.8, Response filed May 6, 2022 to Communication Pursuant to Article 94(3) EPC dated Jan. 5, 2022", 35 pgs.

"European Application Serial No. 21188652.8, Response filed Jul. 4, 2022 to Extended European Search Report dated Nov. 24, 2021", 10 pgs.

\* cited by examiner

SENSOR-BASED PAIN MANAGEMENT SYSTEMS AND METHODS

CLAIM OF PRIORITY

This application is a continuation of U.S. application Ser. No. 17/095,642, filed Nov. 11, 2020, which is a continuation of U.S. application Ser. No. 16/034,304, filed Jul. 12, 2018, now U.S. Pat. No. 10,898,718, which claims the benefit of priority under 35 U.S.C. § 119(e) of U.S. Provisional Patent Application Ser. No. 62/533,789, filed on Jul. 18, 2017, each of which is herein incorporated by reference in its entirety.

CROSS REFERENCE TO RELATED APPLICATIONS

This application is related to commonly assigned U.S. Provisional Patent Application Ser. No. 62/445,075, entitled "PAIN MANAGEMENT BASED ON FUNCTIONAL MEASUREMENTS", filed on Jan. 11, 2017, which is incorporated by reference in their entirety.

TECHNICAL FIELD

This document relates generally to medical systems and more particularly to systems, devices, and methods for pain management.

BACKGROUND

Pain is one of the most common and among the most personally compelling reasons for seeking medical attention, and consumes considerable healthcare resources each year. The relation between etiology, underlying mechanisms and the specific symptoms and signs related to painful disorders is complex. Pain in an individual patient may be produced by more than one mechanism.

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain. Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system).

Chronic pain may be treated or alleviated using medications, acupuncture, surgery, and neuromodulation therapy, among others. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), which can electrically stimulate tissue or nerve centers to treat nervous or muscular disorders. In an example, an IPG can deliver electrical pulses to a specific region in a patient's spinal cord, such as particular spinal nerve roots or nerve bundles, to create an analgesic effect that masks pain sensation.

SUMMARY

By way of example, chronic pain management may involve determining appropriate treatment regimens such as SCS and evaluating therapy efficacy. Accurate pain assessment and characterization are desirable for managing patients with chronic pain. Currently, pain assessment generally relies on patient subjective report of pain symptoms, including severity, pattern, or duration of pain. Based on the patient reported pain sensation, a clinician may prescribe a pain therapy, such as to program an electrostimulator for delivering a neuromodulation therapy. However, the subjective description of pain sensation may be constrained by patient cognitive abilities. The subjective pain description may also be subject to intra-patient variation, such as due to a progression of a chronic disease, or a change in general health status or medication. Having a patient to report and describe each pain episode that he or she has experienced is not efficient, and may delay appropriate pain therapy. Additionally, for patients in an ambulatory setting who lacks immediate access to medical assistance, manual adjustment of pain therapy by a clinician may not be feasible especially if immediate therapy titration is required.

Some sensors may sense patient response to pain and detect onset of a pain episode or worsening of pain. Operating these sensors for pain detection and pain assessment, however, may consume a lot of power and require substantial computing resources, particularly when chronic pain monitoring and assessment is desired. In certain implementations, some sensors may be incorporated into an ambulatory monitor for ambulatory and chronic pain monitoring. The ambulatory monitor usually has limited battery power, storage space, information processing power, and communication bandwidth. These constraints may affect the performance of sensor-based ambulatory pain assessment. Additionally, patient pain may be associated with a patient context, such as when a patient engages in physical activities, or during a certain time of a day. Using the patient context may lead to more efficient sensor usage and improved pain monitoring and assessment. The present inventors have recognized that there remains a demand for apparatus and methods of ambulatory monitoring, sensor-based pain assessment, and automated pain therapy.

This document discusses, among other things, systems, devices, and methods for assessing pain of a subject. The system includes a first sensor circuit to sense from the patient a first signal indicative of a functional state of the patient, a second sensor circuit to sense a second signal different from the first signal, and a controller circuit. The second signal may include a physiological signal or a functional signal. The controller circuit may determine an operating mode of the second sensor circuit using the sensed first signal, trigger the second senor circuit to sense the second signal under the determined operating mode, and generate a pain score using at least the second signal sensed under the determined operating mode. The pain score can be output to a patient or used for closed-loop control of a pain therapy.

Example 1 is a system for managing pain of a patient. The system comprises a first sensor circuit that may sense from the patient a first signal indicative of a functional state of the patient, a second sensor circuit that may sense from the patient a second signal different from the first signal, and a controller circuit. The controller circuit may determine an operating mode of the second sensor circuit using the sensed first signal, trigger the second sensor circuit to sense the second signal under the determined operating mode, and generate a pain score using at least the second signal sensed under the determined operating mode. The system may output the pain score to a user or a process.

In Example 2, the subject matter of Example 1 optionally includes an electrostimulator coupled to the controller circuit that may generate electrostimulation energy to treat pain. The controller circuit may control the electrostimulator to deliver a pain therapy and to control the electrostimulation energy generated by the electrostimulator according to the pain score.

In Example 3, the subject matter of Example 2 optionally includes the electrostimulator that may deliver at least one of: a spinal cord stimulation; a brain stimulation; or a peripheral nerve stimulation.

In Example 4, the subject matter of any one or more of Examples 1-3 optionally includes the first sensor circuit that may be coupled to at least one ambulatory sensor to sense the first signal. The ambulatory sensor may include at least one of: an accelerometer; a gyroscope; a magnetometer; a strain gauge; or a global positioning system sensor.

In Example 5, the subject matter of any one or more of Examples 1-4 optionally includes the first signal that may include a physical activity signal. The controller circuit may trigger the second sensor circuit to sense the second signal under a first operating mode if the physical activity signal falls below an activity threshold, and trigger the second sensor circuit to sense the second signal under a second operating mode different from the first operating mode if the physical activity signal exceeds the activity threshold.

In Example 6, the subject matter of any one or more of Examples 1-4 optionally includes the first signal that may include a physical activity signal. The controller circuit may trigger the second sensor circuit to sense the second signal under a first operating mode if the physical activity signal corresponds to a physical activity template indicative of a physical activity pattern when the patient is free of pain, and trigger the second sensor circuit to sense the second signal under a second operating mode different from the first operating mode if the physical activity signal fails to correspond to the physical activity template.

In Example 7, the subject matter of any one or more of Examples 1-3 optionally includes the first signal that may include a posture signal.

In Example 8, the subject matter of any one or more of Examples 1-3 optionally includes the first signal that may include a gait or a balance signal.

In Example 9, the subject matter of any one or more of Examples 1-3 optionally includes the first signal that may include a range-of-motion signal.

In Example 10, the subject matter of any one or more of Examples 1-9 optionally includes the second signal that may include at least one of: a cardiac electrical activity signal; an electromyography signal; a photoplethysmography signal; a galvanic skin response signal; an electroencephalogram signal; or a hemodynamic signal.

In Example 11, the subject matter of any one or more of Examples 1-10 optionally includes the controller circuit that may determine the operating mode of the second sensor circuit including initiating data acquisition if the sensed first signal satisfies a condition.

In Example 12, the subject matter of any one or more of Examples 1-11 optionally includes the controller circuit that may determine the operating mode of the second sensor circuit including adjusting data acquisition rate if the sensed first signal satisfies a condition.

In Example 13, the subject matter of any one or more of Examples 1-12 optionally includes the control circuit that may generate one or more signal metrics from the sensed second signal under the determined operating mode, and generate the pain score using the generated one or more signal metrics respectively weighted by weight factors.

In Example 14, the subject matter of any one or more of Examples 1-13 optionally includes the control circuit that may generate the pain score further using the sensed first signal.

In Example 15, the subject matter of any one or more of Examples 2-14 optionally includes an implantable neuromodulator device that may include one or more of the first sensor circuit, the second sensor circuit, the controller circuit, or the electrostimulator.

Example 16 is a method for managing pain of a patient using an implantable neuromodulator device. The method comprises steps of: sensing a first signal indicative of a functional state of the patient via a first sensor circuit; determining an operating mode of a second sensor circuit using the sensed first signal; sensing a second signal via the second sensor circuit under the determined operating mode, the second signal different from the first signal; generating a pain score using at least the second signal sensed under the determined operating mode; and outputting the pain score to a user or a process.

In Example 17, the subject matter of Example 16 optionally includes delivering a pain therapy via the implantable neuromodulator device. The pain therapy may include electrostimulation energy determined according to the pain score.

In Example 18, the subject matter of Example 16 optionally includes determining the operating mode of the second sensor circuit, which may include initiating data acquisition if the sensed first signal satisfies a condition.

In Example 19, the subject matter of Example 16 optionally includes determining the operating mode of the second sensor circuit, which may include adjusting data acquisition rate if the sensed first signal satisfies a condition.

In Example 20, the subject matter of Example 16 optionally includes the first signal that may include a physical activity signal. The determining the operating mode of the second sensor circuit may include steps of: comparing the sensed physical activity signal to an activity threshold or to an activity template; initiating data acquisition of the second signal or acquiring the second signal at a first data acquisition rate if the comparison satisfies a first condition; and withholding data acquisition of the second signal or acquiring the second signal at a second, lower data acquisition rate than the first data acquisition rate if the comparison satisfies a second condition indicating a higher physical activity level.

In Example 21, the subject matter of Example 16 optionally includes the first signal that may include at least one of a posture signal, a balance signal, or a range-of-motion signal.

In Example 22, the subject matter of Example 16 optionally includes the second signal that may include at least one of a cardiac electrical activity signal, an electromyography signal, a photoplethysmography signal, a galvanic skin response signal, an electroencephalogram signal, or a hemodynamic signal.

In Example 23, the subject matter of Example 16 optionally includes generating one or more signal metrics from the sensed second signal under the determined operating mode. The generating the pain score includes using the generated one or more signal metrics respectively weighted by weight factors.

The pain score generated based on the functional signals, such as based on the motor activity or sleep state signals as discussed in this document, may improve medical diagnostics of automated characterization of patient pain, as well as individualized therapies to alleviate pain and to reduce side effects. The systems, devices, and methods discussed in this document may also enhance the performance and functionality of a pain management system or device. A device or a system programmed with the sensor-based pain assessment methods improves the automaticity in pain assessment. More efficient device memory or communication bandwidth usage may be achieved by storing or transmitting medical information more relevant to clinical decisions.

The systems and methods for pain assessment that use a first sensor signal to trigger data acquisition and storage of a second sensor signal, as discussed in this document, provide a power- and resource-conservative solution to ambulatory pain monitoring. Operating multiple sensors for pain assessment may put a high demand for battery power, storage space, computing resources, and communication bandwidth on an ambulatory pain monitor. The triggered sensor activation and pain assessment may not only reduce active operation time of the corresponding device components, but also help ensure high-quality sensor data (e.g., a higher data resolution) be collected in a specific patient context (e.g., when the patient engage in a specific physical activity) and used for pain assessment. As such, the systems and methods discussed herein may improve pain assessment accuracy and system efficiency, but at lower operation cost. Additionally, through improved pain therapy based on patient individual need and therapy efficacy, battery longevity of an implantable device may be enhanced, or pain medication volume may be saved.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
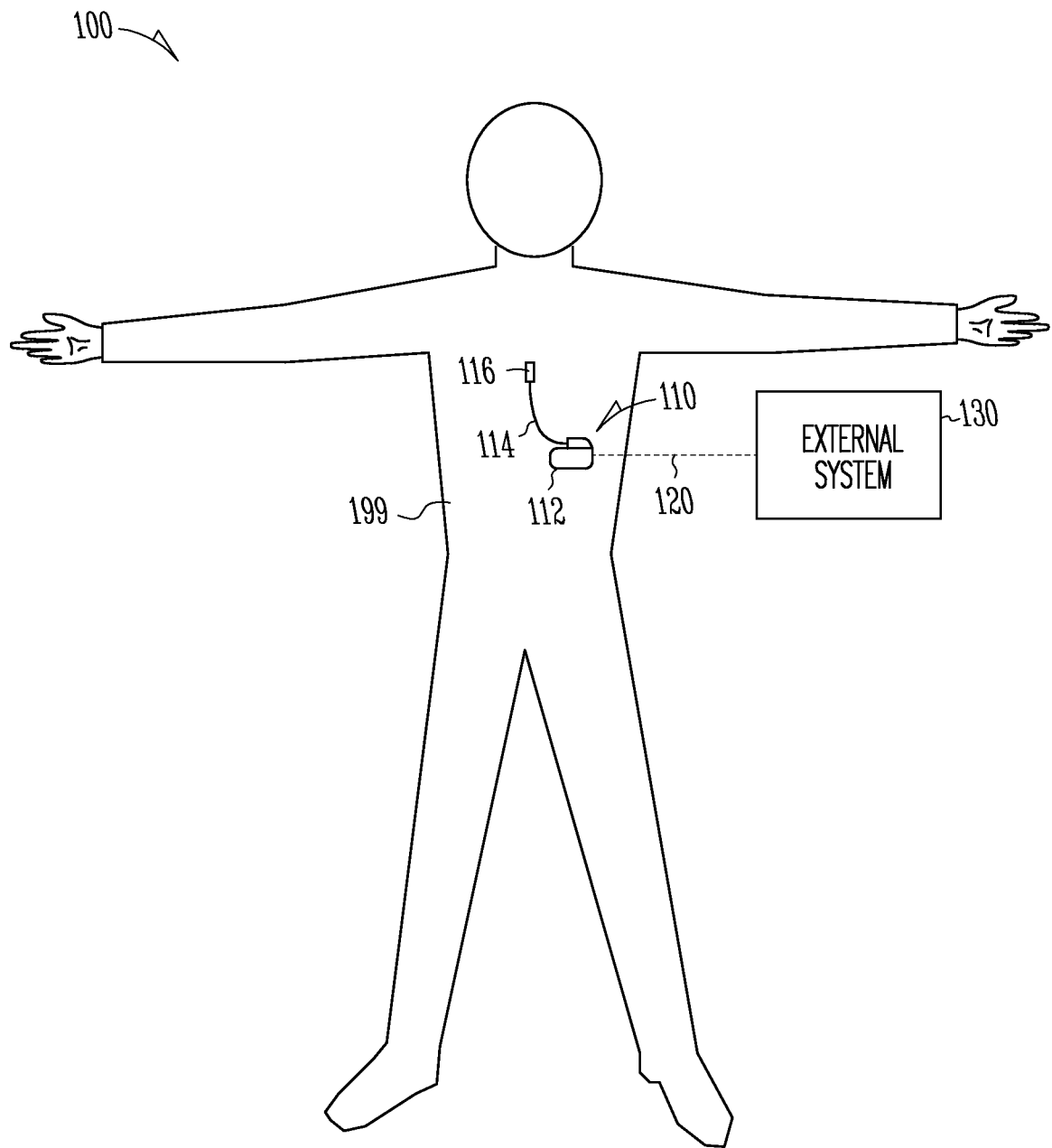
FIG. 1 illustrates, by way of example and not limitation, a neuromodulation system and portions of an environment in which the neuromodulation system may operate.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Clinically, chronic pain may affect a patient's functional state such as motion control. Patient in pain may present with poor or unbalanced posture, abnormal gait pattern, restrained range-of-motion, or decreased intensity or duration of physical activities. Pain may also cause body to compensate, such that muscles, ligaments and nerves may move differently to adapt to the pain. Over time, some muscles may become chronically tight while other muscles weaken, and ligaments may stretch to accommodate uneven body motion. The compensatory changes in posture and the unbalanced motion pattern may gradually exacerbate the chronic pain and cause recurring injuries, resulting in a vicious pain cycle.

Chronic pain may also be associated with changes in patient physiological conditions. Pain may impair neurocardiac integrity. In the presence of pain, elevated sympathetic activity and/or withdrawal of parasympathetic activity may cause cardiovascular reactions, including constriction of peripheral blood vessels, increase in blood pressure, increase in heart rate, decrease in heart rate variability, and increase in cardiac force of contraction, among others. Alterations in autonomic function such as increased sympathetic tone may also affect cardiac electrical activity, such as changes in electrocardiography (ECG) morphology or timing. In another example, chronic pain may be associated with muscle tension. When muscles remain being contracted for an extended period of time, blood flow to the soft tissues, including muscles, tendons, and nerves in the back may be reduced. Close monitoring of patient muscle tension, such as detected from electromyography (EMG) or a mechanical contraction signal, may provide an objective assessment of pain, and may be used to improve pain therapy efficacy.

Disclosed herein are systems, devices, and methods for or assessing pain of a subject, and optionally programming pain therapy based on the pain assessment. In various embodiments, the present system may include a first sensor circuit to sense from the patient a first signal indicative of a functional state of the patient, a second sensor circuit to sense a second signal different from the first signal, and a controller circuit. The second signal may include a physiological signal or a functional signal. The controller circuit that may determine an operating mode of the second sensor circuit using the sensed first signal, trigger the second senor circuit to sense the second signal under the determined operating mode, and generate a pain score using at least the second signal sensed under the determined operating mode. The pain score can be output to a patient or used for closed-loop control of a pain therapy.

The present system may be implemented using a combination of hardware and software designed to provide a closed-loop pain management regimen to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, and Vagus Nerve Stimulation (VNS) therapies. In various examples, instead of providing closed-loop pain therapies, the systems, devices, and methods described herein may be used to monitor the patient and assess pain that either occurs intrinsically, or is induced by nerve block procedures or radiofrequency ablation therapies, among others. The patient monitoring may include generating recommendations to the patient or a clinician regarding pain treatment.

FIG. 1 illustrates, by way of example and not limitation, an example of a neuromodulation system 100 for managing pain of a subject such as a patient with chronic pain, and portions of an environment in which the neuromodulation system 100 may operate. The neuromodulation system 100 may include an implantable system 110 that may be associated with a body 199 of the subject, and an external system 130 in communication with the implantable system 110 via a communication link 120.

The implantable system 110 may include an ambulatory medical device (AMD), such as an implantable neuromodulator device (IND) 112, a lead system 114, and one or more electrodes 116. The IND 112 may be configured for subcutaneous implant in a patient's chest, abdomen, or other parts of the body 199. The IND 112 may be configured as a monitoring and diagnostic device. The IND 112 may include a hermetically sealed can that houses sensing circuitry to sense physiological or functional signals from the patient via sensing electrodes or ambulatory sensors associated with the patient and in communication with the IND 112. In some examples, the sensing electrodes or the ambulatory sensors may be included within the IND 112. The physiological or functional signals, when measured during a pain episode, may be correlative to severity of the pain. The IND 112 may characterize and quantify the pain, such as to determine onset, intensity, severity, duration, or patterns of the pain experienced by the subject. The IND 112 may generate an alert to indicate occurrence of a pain episode, pain exacerbation, or efficacy of pain therapy, and present the alert to a clinician.

The IND 112 may alternatively be configured as a therapeutic device for treating or alleviating the pain. In addition to the pain monitoring circuitry, the IND 112 may further include a therapy unit that can generate and deliver energy or modulation agents to a target tissue. The energy may include electrical, magnetic, or other types of energy. In some examples, the IND 112 may include a drug delivery system such as a drug infusion pump that can deliver pain medication to the patient, such as morphine sulfate or ziconotide, among others.

The IND 112 may include electrostimulation circuitry that generates electrostimulation pulses to stimulate a neural target via the electrodes 116 operably connected to the IND 112. In an example, the electrodes 116 may be positioned on or near a spinal cord, and the electrostimulation circuitry may be configured to deliver SCS to treat pain. In another example, the electrodes 116 may be surgically placed at other neural targets such as a brain or a peripheral neutral tissue, and the electrostimulation circuitry may be configured to deliver brain or peripheral stimulations. Examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic modulation, adrenal gland modulation, baroreceptor stimulation, or transcranial magnetic stimulation, among other peripheral nerve or organ stimulation.

In various examples, the electrodes 116 may be distributed in one or more leads of the lead system 114 electrically coupled to the IND 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IND 112 and tissue of the patient. The neurostimulation pulses are each delivered from the IND 112 through a set of electrodes selected from the electrodes 116. In various examples, the neurostimulation pulses may include one or more individually defined pulses, and the set of electrodes may be individually definable by the user for each of the individually defined pulses.

Although the discussion herein with regard to the neuromodulation system 100 focuses on an implantable device such as the IND 112, this is meant only by way of example and not limitation. It is within the contemplation of the present inventors and within the scope of this document, that the systems, devices, and methods discussed herein may also be used for pain management via subcutaneous medical devices, wearable medical devices (e.g., wrist watch, patches, garment- or shoe-mounted device), or other external medical devices, or a combination of implantable, wearable, or other external devices. The therapy, such as electrostimulation or medical therapies, may be used to treat various neurological disorders other than pain, which by way of example and not limitation may include epilepsy, obsessive compulsive disorder, tremor, Parkinson's disease, or dystonia, among other movement and affective disorders.

The external system 130 may be communicated with the IND 112 via a communication link 120. The external system 130 may include a dedicated hardware/software system such as a programmer, a remote server-based patient management system, or alternatively a system defined predominantly by software running on a standard personal computer. The external system 130 may be configured to control the operation of the IND 112, such as to program the IND 112 for delivering neuromodulation therapy. The external system 130 may additionally receive via the communication link 120 information acquired by IND 112, such as one or more physiological or functional signals. In an example, the external system 130 may determine a pain score based on the physiological or functional signals received from the IND 112, and program the IND 112 to deliver pain therapy in a closed-loop fashion. Examples of the external system and neurostimulation based on pain score are discussed below, such as with reference to FIGS. 2-3.

The communication link 120 may include one or more communication channels and intermediate devices between the external system and the IND, such as a wired link, a telecommunication link such as an internet connection, or a wireless link such as one or more of an inductive telemetry link, a radio-frequency telemetry link. The communication link 120 may provide for data transmission between the IND 112 and the external system 130. The transmitted data may include, for example, real-time physiological or functional signals acquired by and stored in the IND 112, therapy history data, data indicating device operational status of the IND 112, one or more programming instructions to the IND 112 which may include configurations for sensing physiologic signal or stimulation commands and stimulation parameters, or device self-diagnostic test, among others. In some examples, the IND 112 may be coupled to the external system 130 further via an intermediate control device, such as a handheld external remote control device to remotely instruct the IND 112 to generate electrical stimulation pulses in accordance with selected stimulation parameters produced by the external system 130.

Portions of the IND 112 or the external system 130 may be implemented using hardware, software, firmware, or combinations thereof. Portions of the IND 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
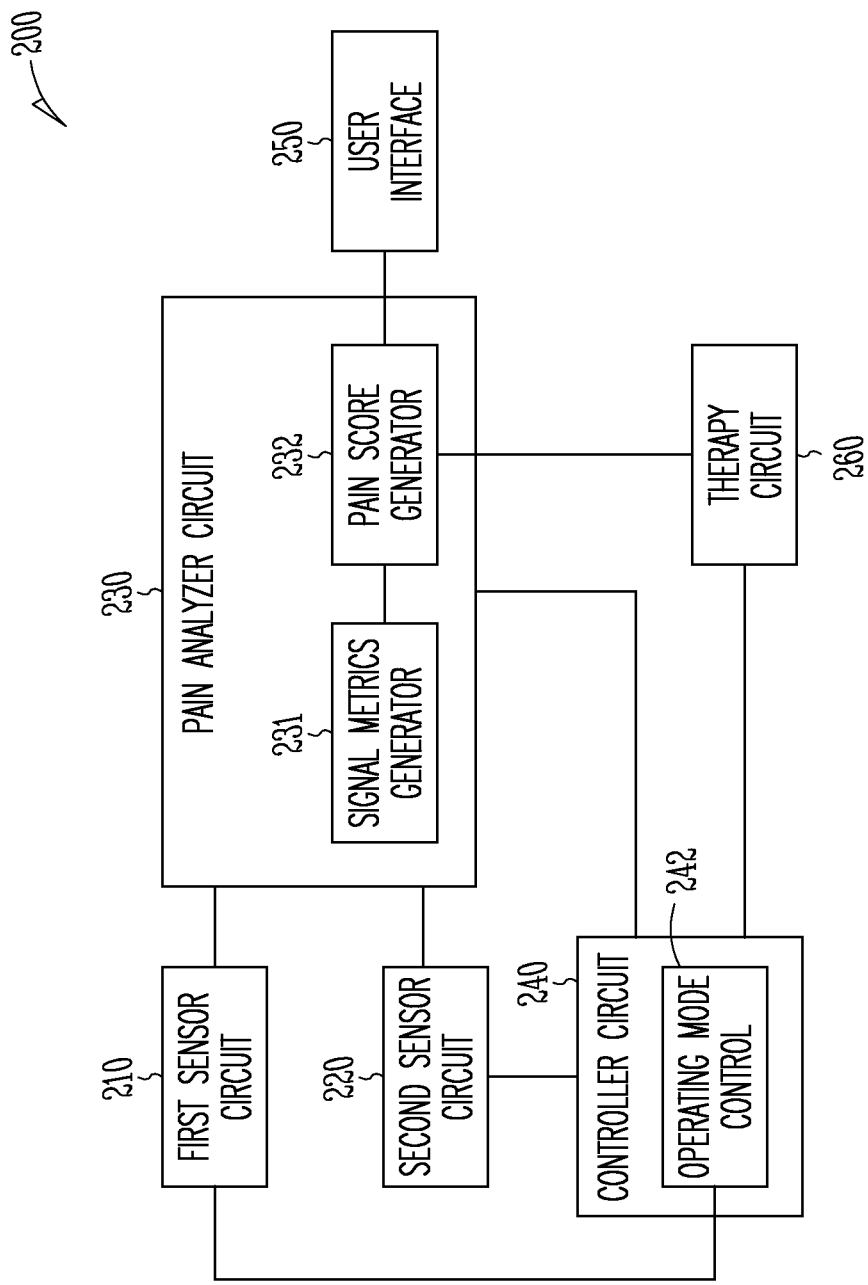
FIG. 2 illustrates, by way of example and not limitation, a block diagram of a pain management system.

FIG. 2 illustrates, by way of example and not limitation, an example of a pain management system 200, which may be an embodiment of the neuromodulation system 100. The pain management system 200 may assess pain of a subject using functional or physiological signals. As illustrated in FIG. 2, the pain management system 200 may include a first sensor circuit 210, a second sensor circuit 220, a pain analyzer circuit 230, a controller circuit 240, and a user interface 250. In some examples, the pain analyzer circuit 230 may be part of the controller circuit 240. The pain management system 200 may additionally include a therapy circuit 260 to deliver pain therapy such as according to the pain assessment.

The first sensor circuit 210 may be configured to sense a first signal indicative of functional state of the subject. The first sensor circuit 210 may be coupled to a motion sensor to sense at least one functional signal. The motion sensor may be an ambulatory sensor, such as an implantable or wearable sensor associated with the patient. Additionally or alternatively, the motion sensor may be a stationary sensor, such as mounted in a room or attached to furniture, to detect one or more functional signals from the patient when the patient enters, or remains within, an environment of patient daily life.

The first sensor circuit 210 may include sense amplifier circuit that may pre-process the sensed signals, including, for example, amplification, digitization, filtering, or other signal conditioning operations. In an example, the functional signal may include a motor activity signal. Examples of the motor activity signal may include, but are not limited to, patient posture, gait, balance, or physical activity signals, among others. In another example, the functional signal may include a sleep state signal that contains information about sleep disturbance. Chronic pain patients may experience frequent disrupted sleep or change of sleep patterns. The motion sensor may detect frequency or duration of sleep position switch, sleep incline, or other indicators of sleep quality. Examples of the sensors for detecting various functional signals are discussed below, such as with reference to FIG. 4.

The second sensor circuit 220 may sense from the subject a second signal different from the first signal sensed from the first sensor circuit 210. The second sensor circuit 220 may be coupled to an ambulatory sensor or a stationary sensor to sense one or more physiological signals or one or more functional signals different from the first signal. The physiological signals may reveal characteristic signal properties in response to an onset, intensity, severity, duration, or patterns of pain. Information of physiological signal changes may be used to assess patient pain.

Pain may impair neuro-cardiac integrity. In the presence of pain, elevated sympathetic activity and/or withdrawal of parasympathetic activity may cause cardiovascular reactions, such as increased heart rate, enhanced cardiac force, and changes in electrical activity. Examples of the cardiac signals can include a heart rate signal, a pulse rate signal, a heart rate variability signal, electrocardiograph (ECG) or intracardiac electrogram, cardiovascular pressure signal, or heart sounds signal, among others.

In addition to or in lieu of the cardiac signals, the second sensor circuit 220 may sense one or more of a galvanic skin response (GSR) signal, an electrodermal activity (EDA) signal, a skin temperature signal, an electromyogram (EMG) signal, an electroencephalogram (EEG) signal, a magnetoencephelogram (MEG) signal, a hemodynamic signal such as a blood flow signal, a blood pressure signal, a blood perfusion signal, a photoplethysmography (PPG) signal, a heart sound signal, or a saliva production signal indicating the change of amount of saliva production, among others. The physiological signals may additionally include pulmonary, neural, or biochemical signals. Examples of pulmonary signals may include a respiratory signal, a thoracic impedance signal, or a respiratory sounds signal. Examples of biochemical signals may include blood chemistry measurements or expression levels of one or more biomarkers, which may include, by way of example and not limitation, B-type natriuretic peptide (BNP) or N-terminal pro b-type natriuretic peptide (NT-proBNP), serum cytokine profiles, P2X4 receptor expression levels, gamma-aminobutyric acid (GABA) levels, TNFα and other inflammatory markers, cortisol, adenosine, Glial cell-derived neurotrophic factor (GDNF), Nav 1.3, Nav 1.7, or Tetrahydrobiopterin (BH4) levels, among other biomarkers.

The pain analyzer circuit 230 may generate a pain score using at least the second signal received from the second sensor circuit 220. In some examples, the pain analyzer circuit 230 generate the pain score further using the functional signal sensed from the first sensor circuit 210. The pain analyzer circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

As illustrated in FIG. 2, the pain analyzer circuit 230 may be coupled to a controller circuit 240 that controls the sensor-based pain assessment. In some examples, the pain analyzer circuit 230 may be part of the controller circuit 240.

The controller circuit 240 may receive the first signal sensed from the first sensor circuit 210. The controller circuit 240 includes an operating mode control 242 that may determine an operating mode of the second sensor circuit 220 using the received first signal. The operating mode controls the data acquisition and data processing at the second sensor circuit 220, and may include an activation or deactivation of sensor data acquisition, or a data acquisition rate such as a sampling rate or a digitization resolution. Using the first sensor signal to trigger activation and to set an operating mode of the second sensor may help improve system or device function of chronic and ambulatory. Activation and operation of multiple sensors for physiological data acquisition can be power- and memory-demanding, and pain assessment may require substantial amount of computing resource. The activation of and operating mode triggered by the first sensor, such as controlled by the controller circuit 240, may reduce the activation time of the second sensor, conserve the device power and computing resources, and thus reduces the operational cost.

The operating mode control 242 may compare the first signal to a condition, such as a threshold or a value range. Based on the comparison, the operating mode control 242 may determine the operating mode of the second sensor circuit 220, such as whether to activate or deactivate data acquisition, time of data acquisition, or a sampling rate for acquiring the second signal. The comparison may indicate an onset of a pain episode or worsening of pain. Activating the data acquisition of the second signal and pain assessment using the second signal may more reliably confirm the pain episode or the worsening of pain. In some examples, the comparison may additionally or alternatively be used to prescreen the second sensor to determine a proper time to acquire data such as to avoid interferences or noise. This may allow for high-quality data being used in pain assessment. Examples of setting the operating mode of the second sensor circuit using the first sensed signal are discussed as follows, such as with reference to FIG. 4.

The pain analyzer circuit 230 and the controller circuit 240 may each include respective circuit sets comprising one or more other circuits or sub-circuits. In an example as illustrated in FIG. 2, the pain analyzer circuit 230 may comprise a signal metric generator 231 and a pain score generator 232. These circuits or sub-circuits may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The signal metric generator 231 may generate one or more signal metrics from the sensed second signal under the determined operating mode. The signal metrics may include statistical parameters extracted from the sensed signal, such as signal mean, median, or other central tendency measures or a histogram of the signal intensity, among others. The signal metrics may additionally or alternatively include morphological parameters such as maximum or minimum within a specific time period such as a cardiac cycle, positive or negative slope or higher order statistics, or signal power spectral density at a specific frequency range, among other morphological parameters. The signal metrics may additionally include timing information such as a time interval between a first characteristic point in one signal and a second characteristic point in another signal. In various examples, the signal metric generator 231 may extract from the second signal, sensed under the determined operating mode, one or more ECG metrics such as heart rate, heart rate variability, timing relationship between characteristic ECG components (e.g., P wave to R wave intervals), PPG metrics, blood pressure metrics, pulse wave transit metrics, EMG metrics, muscle tightness metrics, muscle shortening metrics, EEG metrics, GSR metrics, among others. In some examples, the signal metric generator circuit 231 may additionally generate from the sensed first signal a plurality of functional signal metrics indicative of patient functional state such as motor control or kinetics. By way of example and not limitation, the motor activity metrics may include metrics of posture, gait, physical activity, balance, or range-of-motion.

The pain score generator 232 may generate a pain score using the signal metrics generated from the second signal sensed under the determined operating mode, or optionally along with the signal metrics generated from the first functional signal metrics. The pain score can be represented as a numerical or categorical value that quantifies the patient's overall pain symptom. In an example, a composite signal metric may be generated using a combination of a plurality of the signal metrics respectively weighted by weight factors. The combination can be linear or nonlinear. The pain score generator 232 may compare the composite signal metric to one or more threshold values or range values, and assign a corresponding pain score (such as numerical values from 0 to 10) based on the comparison.

In another example, the pain score generator 232 may compare the signal metrics to their respective threshold values or range values, assign corresponding signal metric-specific pain scores based on the comparison, and compute a composite pain score using a linear or nonlinear fusion of the signal metric-specific pain scores weighted by their respective weight factors. In an example, the threshold can be inversely proportional to signal metric's sensitivity to pain. A signal metric that is more sensitive to pain may have a corresponding lower threshold and a larger metric-specific pain score, thus plays a more dominant role in the composite pain score than another signal metric that is less sensitive to pain. Examples of the fusion algorithm may include weighted averages, voting, decision trees, or neural networks, among others. The pain score generated by the pain score generator 232 may be output to a system user or a process.

The user interface 250 may include an input circuit and an output circuit. In an example, at least a portion of the user interface 250 may be implemented in the external system 130. The input circuit may enable a system user to program the parameters used for sensing the physiological signals, generating signal metrics, or generating the pain score. The input circuit may be coupled to one or more input devices such as a keyboard, on-screen keyboard, mouse, trackball, touchpad, touch-screen, or other pointing or navigating devices. In some example, the input device may be incorporated in a mobile device such as a smart phone or other portable electronic device with a mobile application ("App"). The mobile App may enable a patient to provide pain description or quantified pain scales during the pain episodes. In an example, the input circuit may enable a user to confirm, reject, or edit the programming of the therapy circuit 260, such as parameters for electrostimulation, as to be discussed in the following.

The output circuit may be coupled to a display to present to a system user such as a clinician the pain score, physiological and functional signals sensed from the sensor circuits 210 and 220, trends of the signal metric, or any intermediary results for pain score calculation such as the signal metric-specific pain scores. In some examples, a clinician may assess efficacy of paint treatment using the sensed physiological and functional signals. For example, a patient may become too active too quickly after improvement in pain symptoms or having pain relief. The output of the functional signal such as physical activity trend may aid a clinician in advising the patient to decrease activity or to track an acceptable activity routine through the treatment process. The information may be presented in a table, a chart, a diagram, or any other types of textual, tabular, or graphical presentation formats, for displaying to a system user. The presentation of the output information may include audio or other human-perceptible media format. In an example, the output circuit may generate alerts, alarms, emergency calls, or other means of warnings to signal the system user about the detected pain score.

The therapy circuit 260 may be configured to deliver a therapy to the patient based on the pain score generated by the pain score generator 232. The therapy circuit 260 may include an electrostimulator configured to generate electrostimulation energy to treat pain, or to alleviate side effects introduced by the electrostimulation of the target tissue. In an example, the electrostimulator may deliver spinal cord stimulation (SCS) via electrodes electrically coupled to the electrostimulator. The electrodes may be surgically placed at a region at or near a spinal cord tissue, which may include, by way of example and not limitation, dorsal column, dorsal horn, spinal nerve roots such as the dorsal nerve root, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator may additionally or alternatively deliver electrostimulation to other target tissues such as peripheral nerves tissues. In an example, the electrostimulator may deliver transcutaneous electrical nerve stimulation (TENS) via detachable electrodes that are affixed to the skin. Other examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic modulation, adrenal gland modulation, baroreceptor stimulation, or transcranial magnetic stimulation, among other peripheral nerve or organ stimulation.

The therapy circuit 260 may additionally or alternatively include a drug delivery system, such as an intrathecal drug delivery pump that may be surgically placed under the skin, which may be programmed to inject medication through a catheter to the area around the spinal cord. Other examples of drug delivery system may include a computerized patient-controlled analgesia pump that may deliver the prescribed pain medication to the patient such as via an intravenous line.

The controller circuit 240 may control the therapy circuit 260 to generate and deliver pain therapy, such as neurostimulation energy, according to the pain score received from the pain score generator 232. The controller circuit 240 may control the generation of electrostimulation pulses according to specific stimulation parameters. Additionally or alternatively, the controller circuit 240 may control the therapy circuit 260 to deliver electrostimulation pulses via specific electrodes. In an example of pain management via SCS, a plurality of segmented electrodes, such as the electrodes 116, may be distributed in one or more leads. The controller circuit 240 may configure the therapy circuit 260 to deliver electrostimulation pulses via a set of electrodes selected from the plurality of electrodes. The electrodes may be manually selected by a system user or automatically selected based on the pain score.

Figure 3:
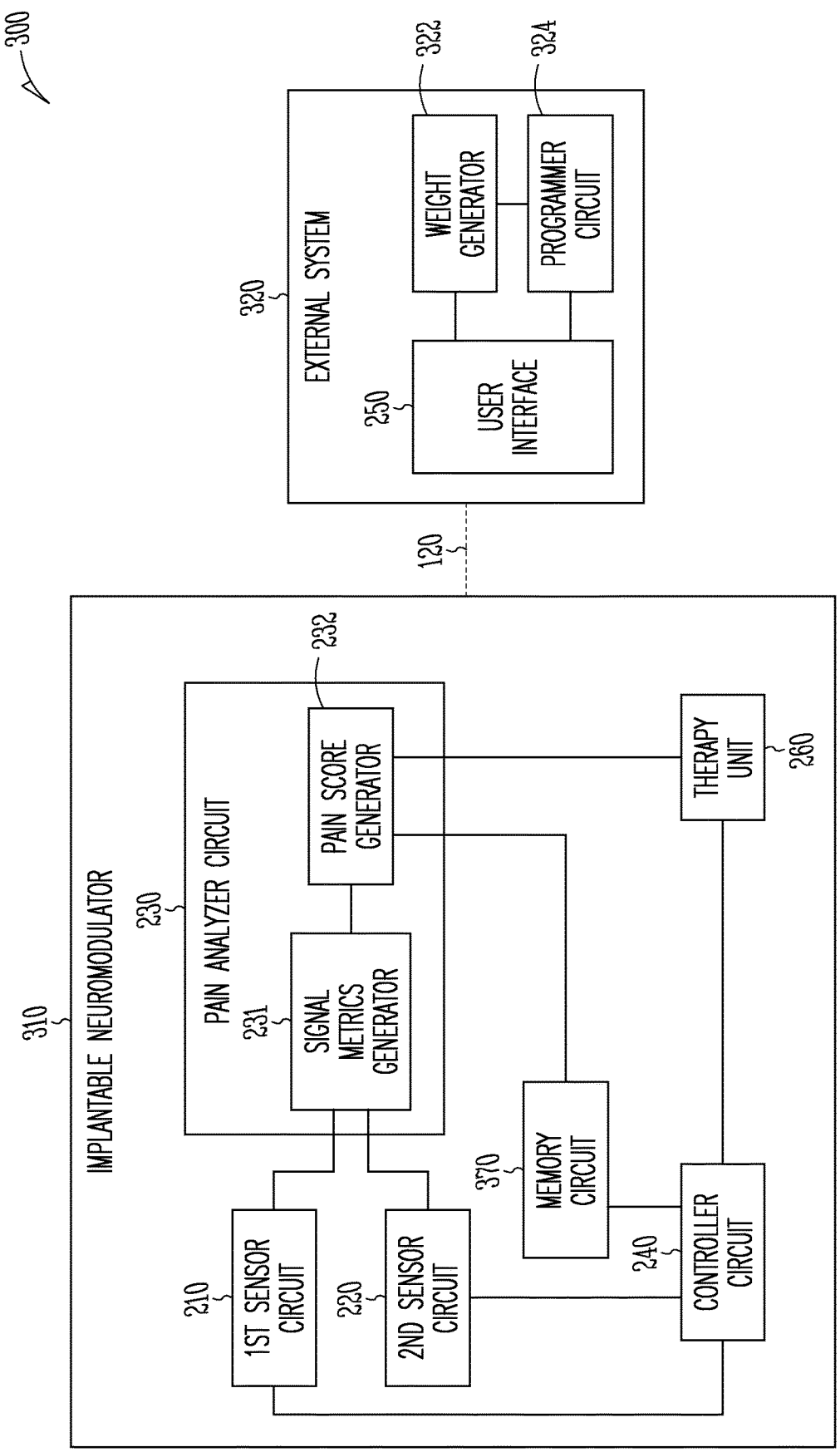
FIG. 3 illustrates, by way of example and not limitation, a block diagram of another pain management system.

FIG. 3 illustrates, by way of example and not limitation, another example of a pain management system 300, which may be an embodiment of the neuromodulation system 100 or the pain management system 200. The pain management system 300 may include an implantable neuromodulator 310 and an external system 320, which may be, respectively, embodiments of the IND 112 and the external system 130 as illustrated in FIG. 1. The external system 320 may be communicatively coupled to the implantable neuromodulator 310 via the communication link 120.

The implantable neuromodulator 310 may include several components of the pain management system 200 as illustrated in FIG. 2, including the first sensor circuit 210, the second sensor circuit 220, the pain analyzer circuit 230, the controller circuit 240, and the therapy circuit 260. As previously discussed, in some examples, the pain analyzer circuit 230 may be part of the controller circuit 240. The implantable neuromodulator 310 may include a memory circuit 370 configured to store sensor signals or signal metrics such as generated by the first sensor circuit 210, the second sensor circuit 220, the signal metric generator 231, and the pain scores such as generated by the pain score generator 232. Data storage at the memory circuit 370 may be continuous, periodic, or triggered by a user command or a specific event. The memory circuit 370 may store weight factors used for generating the composite pain score, such as at the pain score generator 232. The weight factors may be provided by a system user, or alternatively be automatically determined or adjusted such as based on the corresponding signal metrics' reliability in representing an intensity of the pain.

The controller circuit 240 may control the generation of electrostimulation pulses according to specific stimulation parameters. The stimulation parameters may be provided by a system user. Alternatively, the stimulation parameters may be automatically determined based on the intensity, severity, duration, or pattern of pain, which may be subjectively described by the patient, or automatically quantified based on the signals sensed by the sensor circuits 210 and 220. For example, when a patient-described or sensor-indicated pain quantification exceeds a respective threshold value or falls within a specific range indicating elevated pain, the electrostimulation energy may be increased to provide stronger pain relief. Increased electrostimulation energy may be achieved by programming a higher pulse intensity, a higher frequency, or a longer stimulation duration or "on" cycle, among others. Conversely, when a patient-described or sensor-indicated pain quantification falls below a respective threshold value or falls within a specific range indicating no pain or mild pain, the electrostimulation energy may be decreased.

The implantable neuromodulator 310 may receive the information about electrostimulation parameters and the electrode configuration from the external system 320 via the communication link 120. Additional parameters associated with operation of the therapy circuit 260, such as battery status, lead impedance and integrity, or device diagnostic of the implantable neuromodulator 310, may be transmitted to the external system 320. The controller circuit 240 may control the generation and delivery of electrostimulation using the information about electrostimulation parameters and the electrode configuration from the external system 320. Examples of the electrostimulation parameters and electrode configuration may include: temporal modulation parameters such as pulse amplitude, pulse width, pulse rate, or burst intensity; morphological modulation parameters respectively defining one or more portions of stimulation waveform morphology such as amplitude of different phases or pulses included in a stimulation burst; or spatial modulation parameters such as selection of active electrodes, electrode combinations which define the electrodes that are activated as anodes (positive), cathodes (negative), and turned off (zero), and stimulation energy fractionalization which defines amount of current, voltage, or energy assigned to each active electrode and thereby determines spatial distribution of the modulation field.

In an example, the controller circuit 240 may control the generation and delivery of electrostimulation in a closed-loop fashion by adaptively adjusting one or more stimulation parameters or stimulation electrode configuration based on the pain score. For example, if the score exceeds the pain threshold (or falls within a specific range indicating an elevated pain), then the first electrostimulation may be delivered. Conversely, if the composite pain score falls below a respective threshold value (or falls within a specific range indicating no pain or mild pain), then a second pain therapy, such as second electrostimulation may be delivered. The first electrostimulation may differ from the second electrostimulation with respect to at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. In an example, the first electrostimulation may have higher energy than the second electrostimulation, such as to provide stronger effect of pain relief. Examples of increased electrostimulation energy may include a higher pulse intensity, a higher frequency, or a longer stimulation duration or "on" cycle, among others.

The parameter adjustment or stimulation electrode configuration may be executed continuously, periodically at specific time, duration, or frequency, or in a commanded mode upon receiving from a system user a command or confirmation of parameter adjustment. In some examples, the closed-loop control of the electrostimulation may be further based on the type of the pain, such as chronic or acute pain. In an example, the pain analyzer circuit 230 may trend the signal metric over time to compute an indication of abruptness of change of the signal metrics, such as a rate of change over a time period. The pain episode may be characterized as acute pain if the signal metric changes abruptly (e.g., the rate of change of the signal metric exceeding a threshold), or as chronic pain if the signal metric changes gradually (e.g., the rate of change of the signal metric falling below a threshold). The controller circuit 240 may control the therapy circuit 260 to deliver, withhold, or otherwise modify the pain therapy in accordance with the pain type. For example, incidents such as toe stubbing or bodily injuries may cause abrupt changes in certain signal metrics, but no adjustment of the closed-loop pain therapy is deemed necessary. On the contrary, if the pain analyzer circuit 230 detects chronic pain characterized by gradual signal metric change, then the closed-loop pain therapy may be delivered accordingly.

The external system 320 may include the user interface 250, a weight generator 322, and a programmer circuit 324. The weight generator 322 may generate weight factors used by the pain score generator 232 to generate the pain score. The weight factors may indicate the signal metrics' reliability in representing an intensity of the pain. A sensor metric that is more reliable, or more sensitive or specific to the pain, would be assigned a larger weight than another sensor metric that is less reliable, or less sensitive or specific to the pain. In an example, the weight factors may be proportional to correlations between a plurality of quantified pain scales (such as reported by a patient) and measurements of the measurements of the signal metrics corresponding to the plurality of quantified pain scales. A signal metric that correlates with the pain scales is deemed a more reliable signal metric for pain quantification, and is assigned a larger weight factor than another signal metric less correlated with the quantified pain scales. In another example, the weight generator 322 may determine weight factors using the signal sensitivity to pain. The signal metrics may be trended over time, such as over approximately six months. The signal sensitivity to pain may be represented by a rate of change of the signal metrics over time during a pain episode. The signal sensitivity to pain may be evaluated under a controlled condition such as when the patient posture or activity is at a specific level or during specific time of the day. The weight generator 322 may determine weight factors to be proportional to signal metric's sensitivity to pain.

The programmer circuit 324 may produce parameter values for operating the implantable neuromodulator 310, including parameters for sensing the signals and generating signal metrics, and parameters or electrode configurations for electrostimulation. In an example, the programmer circuit 324 may generate the stimulation parameters or electrode configurations for SCS based on the pain score produced by the pain score generator 232. Through the communication link 120, the programmer circuit 324 may continuously or periodically provide adjusted stimulation parameters or electrode configuration to the implantable neuromodulator 210. By way of non-limiting example and as illustrated in FIG. 3, the programmer circuit 324 may be coupled to the user interface 250 to allow a user to confirm, reject, or edit the stimulation parameters, sensing parameters, or other parameters controlling the operation of the implantable neuromodulator 210. The programmer circuit 324 may also adjust the stimulation parameter or electrode configuration in a commanded mode upon receiving from a system user a command or confirmation of parameter adjustment.

The programmer circuit 324, which may be coupled to the weight generator 322, may initiate a transmission of the weight factors generated by the weight generator 322 to the implantable neuromodulator 310, and store the weight factors in the memory circuit 370. In an example, the weight factors received from the external system 320 may be compared to previously stored weight factors in the memory circuit 370. The controller circuit 240 may update the weight factors stored in the memory circuit 370 if the received weight factors are different from the stored weights. The pain analyzer circuit 230 may use the updated weight factors to generate a pain score. In an example, the update of the stored weight factors may be performed continuously, periodically, or in a commanded mode upon receiving a command from a user.

In some examples, the pain score may be used by a therapy unit (such as an electrostimulator) separated from the pain management system 300. In various examples, the pain management system 300 may be configured as a monitoring system for pain characterization and quantification without delivering closed-loop electrostimulation or other modalities of pain therapy. The pain characterization and quantification may be provided to a system user such as the patient or a clinician, or to a process including, for example, an instance of a computer program executable in a microprocessor. In an example, the process includes computer-implemented generation of recommendations or an alert to the system user regarding pain medication (e.g., medication dosage and time for taking a dose), electrostimulation therapy, or other pain management regimens. The therapy recommendations or alert may be based on the pain score, and may be presented to the patient or the clinician in various settings including in-office assessments (e.g. spinal cord stimulation programming optimization), in-hospital monitoring (e.g. opioid dosing during surgery), or ambulatory monitoring (e.g. pharmaceutical dosing recommendations).

In an example, in response to the pain score exceeding a threshold that indicates an elevated pain symptom, an alert may be generated and presented at the user interface 250 to remind the patient to take pain medication. In another example, therapy recommendations or alerts may be based on information about wearing-off effect of pain medication, which may be stored in the memory circuit 370 or received from the user interface 250. When the drug effect has worn off, an alert may be generated to remind the patient to take another dose or to request a clinician review of the pain prescription. In yet another example, before a pain therapy such as neurostimulation therapy is adjusted (such as based on the pain score) and delivered to the patient, an alert may be generated to forewarn the patient or the clinician of any impending adverse events. This may be useful as some pain medication may have fatal or debilitating side effects. In some examples, the pain management system 300 may identify effect of pain medication addiction such as based on functional and physiological signals. An alert may be generated to warn the patient about effects of medication addiction and thus allow medical intervention.

Figure 4:
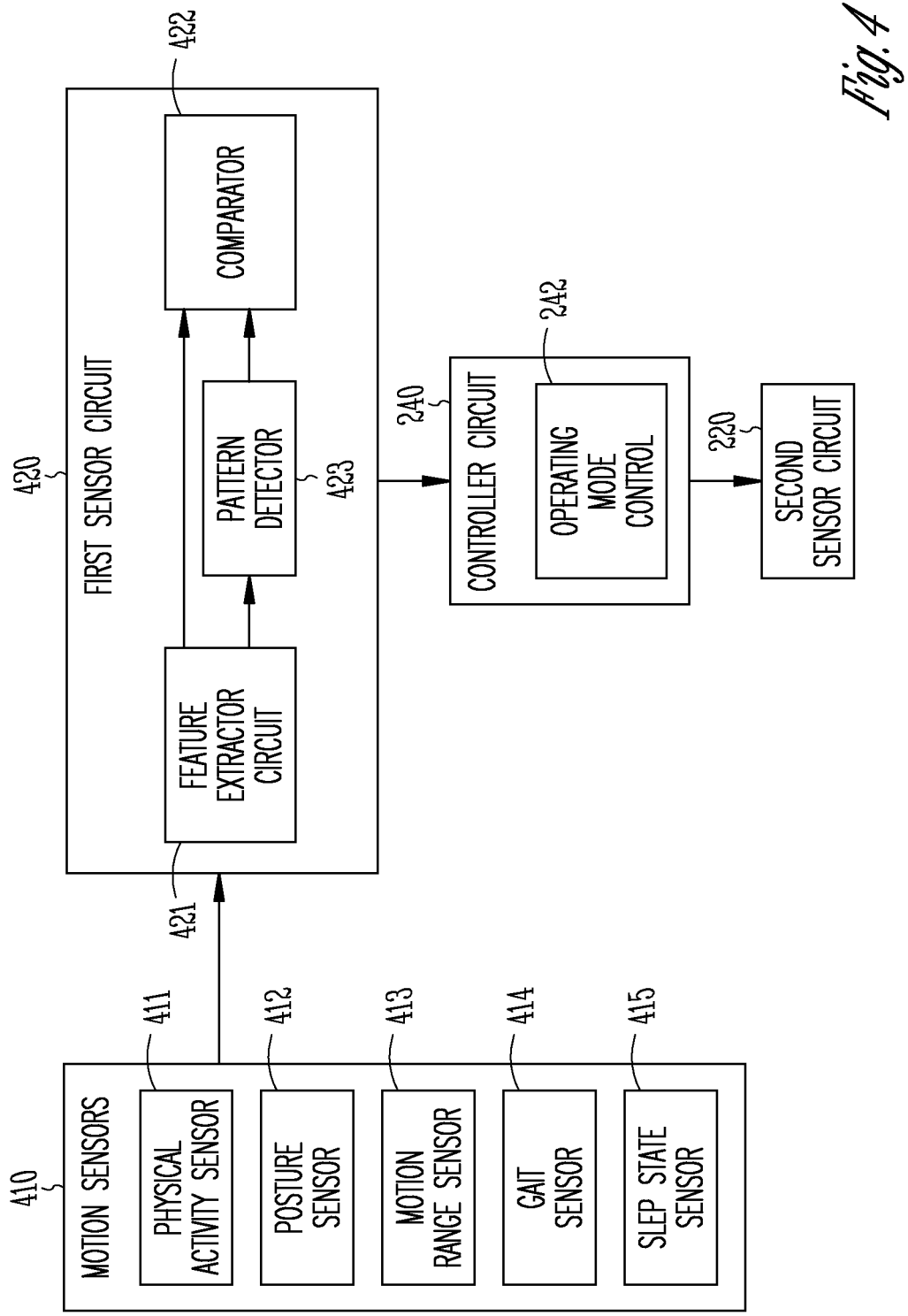
FIG. 4 illustrates, by way of example and not limitation, a portion of a pain management system for setting the operating mode of a second sensor circuit using a signal sensed from a first sensor circuit.

FIG. 4 illustrates, by way of example and not limitation, an example of a portion of a pain management system for setting the operating mode of the second sensor circuit 220 using a signal sensed from a first sensor circuit 420. The system portion may include one or more motion sensors 410, a first sensor circuit 420 which an embodiment of the first sensor circuit 210, the controller circuit 240, and the signal second sensor circuit 220. The signals acquired at the second sensor circuit 220 under the operating mode may be used by the pain management system 200 or 300 to characterize and quantify patient.

By way of example and not limitation, the motion sensors 410 may include one or more of sensors 411-415 that may sense patient functional state. The physical activity sensor 411 may include an accelerometer configured to sense a physical activity signal. The accelerometer may be single-axis or multi-axis accelerometer. The posture sensor 412 may include a tilt switch or a single- or multi-axis accelerometer associated with the patient. For example, the posture sensor may be disposed external to the body or implanted inside the body. Posture may be represented by, for example, a tilt angle. In some examples, posture or physical activity information may be derived from thoracic impedance information. The motion range sensor 413 may include an accelerometer positioned on patient extremities or patient body trunk to detect a range-of-motion. The gait sensor 414 may detect patient gait or a state of balance. Examples of the gait sensors may include accelerometer, gyroscope (which may be a one-, two-, or three-axis gyroscope), magnetometer (e.g., a compass), inclinometers, goniometers, electromagnetic tracking system (ETS), a global positioning system (GPS) sensor, sensing fabric, force sensor, strain gauges, and sensors for electromyography (EMG). The sensors may be configured for wearing at, or attaching to, patient foot, ankle, leg, waist, or other parts on the torso or the extremities. In an example, the gait sensor 414 may include an insole force sensor for placement inside a shoe or a boot. The insole force sensor may take the form of a strain gauge, a piezoelectric sensor, or a capacitive sensor, among others. The insole force sensor may be wirelessly coupled to the IND 310 or the pain analyzer circuit 230. The first sensor circuit 210 may analyze force distribution on a patient's foot, and generate an indicator of gait. The sleep state sensor 415 may include an accelerometer, a piezoelectric sensor, biopotential electrodes and sensors, or other sensors to detect the sleep state of the patient.

The motion sensors 410 may be associated with a patient in various manners. In an example, one or more of the motion sensors 410 may be implantable sensors configured for subcutaneous implantation at various body locations. One or more of the motion sensors 410 may be wearable sensors configured to be worn on the head, wrist, hand, foot, ankle, waist, or other parts of the body, or apparel-mounted sensor that may be mounted on a garment, a footwear, a headwear, or one or more accessories carried by the patient, such as a pendant, a necklace, or a bracelet. In another example, one or more of the motion sensors 410 may be stationary sensors configured for placement in patient environment, such as at a bedside, in a room at patient home, or in a testing room at a clinic or medical facility. In an example, the motion sensors may be mounted on a chair, a bed (e.g., under or attached to a mattress), or a fixture in a patient's environment. Unlike the implantable, wearable, or apparel-mounted sensors which are ambulatory in nature, the stationary sensors are configured to detect one or more functional signals when the patient enters, or remains within, an environment within the scope of surveillance of the stationary sensor. In an example, the stationary sensors may include a camera or a video recorder configured to capture an image, an image sequence, or a video of the patient at a specific physical state, such as sitting, standing, walking, or doing physical activities. In an example, the camera may be an infrared camera. In an example, the camera is a digital camera that may generate digital data representation of an image or a video sequence.

In some examples, one or more of the motion sensors 410 may be incorporated in a mobile device, such as a smart phone, a wearable device, a fitness band, a portable health monitor, a tablet, a laptop computer, among other portable computerized device. For example, one or more of an accelerometer, a gyroscope, a magnetometer, a GPS sensor, or a camera that sense motor activity signals may be embedded in a mobile device. The mobile device may be communicatively coupled to the IND 310 or the pain analyzer circuit 230 via a communication link such as a universal serial bus connection, a Bluetooth protocol, Ethernet, IEEE 802.11 wireless, an inductive telemetry link, or a radio-frequency telemetry link, among others.

The first sensor circuit 420, an embodiment of the first sensor circuit 210, may be coupled to the motion sensors 410 via wired or wireless connections. The first sensor circuit 420 may include a sense amplifier circuit that may preprocess the sensed functional signal, and a feature extractor circuit 421 that may extract one or more motor activity features from the processed functional signals. In an example, features extracted from the physical activity signal may include one or more of activity intensity, activity duration, or a transition time between different types of activities. A decrease in activity intensity or duration from an activity baseline such as established using patient historical activity signals, or less frequent transition or an increase in transition time from one activity to another may indicate pain suffered by the patient. In another example, features extracted from the posture signal may include body position during sitting, standing, or walking. A decrease in activity intensity or duration from an activity baseline such as established using patient historical activity signals, or less frequent transition or an increase in transition time from one activity to another may indicate pain suffered by the patient. In an example, features extracted from the motion range signal may include lumbar forward flexion, shoulder flexion, elbow flexion, rotation of arm and elbow joint, trunk-pelvis rotation, or other motor control and kinematic features. The motion range feature may include indication of smoothness of motion, such as a rate or a pattern of change in motion with respect to time, or with respect to angular velocity, etc. In another example, features extracted from the gait signal or balance signal may include velocity, time to peak velocity, step length, stride length, stride width, swing time, single limb support time, double limb stance, gait autonomy, cadence, among other measurements. In yet another example, features extracted from the sleep state signal may include sleep incline, sleep sidedness, frequency of sleep position switch, or other sleep quality or sleep disturbance metrics. For example, an increase in sleep incline, or enhanced frequency of body position switches during sleep, or reduced sleep duration are indicators of increase pain. The sleep state features, when satisfying a condition that indicates occurrence or aggravation of a pain episode, may trigger one or more other sensors to sense physiological or functional signals. In an example, if the frequency of sleep position switch exceeds a threshold, or if the sleep duration at a sleep position falls below a threshold (e.g., less than 5-15 seconds), sleep disturbance is indicated, which may trigger other sensors for sensing heart rate, respiration rate, jaw clench, or other physiological or functional responses. The sensed response may be used to distinguish between normal sleep patterns (e.g., sleep position change) and abnormal sleep patterns caused by or otherwise associated with acute pain.

Measurements of the extracted feature may be trended over time. The comparator 422 may compare the extracted feature trend to one or more thresholds or one or more value ranges to determine patient functional state. The operating mode control 242 in the controller circuit 240 may determine an operating mode for the second sensor circuit 220 according to the comparison. In an example, the comparator 422 may compare one or more features extracted from the physical activity signal to determine patient physical activity level. Physical activity level may indicate presence or severity of pain. Patient in pain are generally less active, such that periods of activity are generally shorter and activity intensity is generally lower. If the comparison at the comparator 422 indicates a low physical activity level (in activity intensity or duration), then a pain episode or precursor of pain has likely occurred. The operating mode control 242 may activate the second sensor circuit 220 to initiate sensing signals such as cardiac, pulmonary, muscular, or neurological signals. However, if the comparison at the comparator 422 indicates a high physical activity level, then the patient is not likely experiencing pain. The operating mode control 242 may at least temporarily deactivate the second sensor circuit 220 from sensing data if the second sensor circuit 220 is in an active data-acquisition mode, or control the second sensor circuit 220 to withhold data acquisition.

In some examples, the extracted feature of physical activity may be measured during a specified time period of daytime or nighttime, or in a specific context such as when the patient is asleep. For example, if a high physical activity level is detected by the comparator 422 using the physical activity features extracted during a period of nighttime, or the high physical activity level is accompanied a detection of sleep such as detected by the sleep state sensor 415, the detected high physical activity level may indicate an onset of pain, worsening of pain, or undesirable pain treatment. The operating mode control 242 may activate the second sensor circuit 220 or acquire the data at a high data acquisition rate.

The first sensor circuit 422 may include a pattern detector 423 to detect a physical activity pattern using measurements of the extracted feature over time, such as collected within a specific time period during daytime or nighttime. The activity pattern may indicate the temporal variation of the physical activity during the specific time period. The comparator 422 may compare the detected physical activity pattern to a physical activity template representing a physical activity pattern under a known, controlled condition, such as a baseline pain-free condition. The physical activity template may be generated using the historical activity data from the same patient, or using activity data from a patient population. The comparator 422 may compute a dissimilarity measure, such as a distance measure, between the detected physical activity pattern and the physical activity template representing activity pattern during a pain-free condition. For example, pain patients tend to decrease activity during the course of a day, while healthy subjects generally have more stable daily activity levels. The pattern detector 423 may compute a decay rate of activity level during a time period (such as during a 12-hour period from morning to evening), and the comparator 422 may determine a dissimilarity of the decay rate of the detected physical activity and the decay rate of the physical activity template. If the dissimilarity exceeds a threshold, then the detected physical activity pattern indicates a high likelihood of pain. The operating mode control 242 may activate the second sensor circuit 220, or acquire the data at a high data rate mode. In some examples, the physical activity template may represent physical activity pattern under other known conditions, such as when the patient is in pain, walking, sitting still, or any other form of activity. In another example, the physical activity template may represent patient regular activity (e.g. daily jog) during a particular period of day. If the comparator 422 determines a dissimilarity measure indicating that the regularly activity is missing from the detected physical activity pattern at the particular period of day, it may indicate that the patient is experiencing pain, which causes an absence of regular activity. The operating mode control 242 may activate the second sensor circuit 220, or acquire the data at a high data rate mode.

In addition to or in lieu of activation or deactivation of the second sensor circuit 220, the operating mode control 242 may adjust data acquisition rate of the second sensor circuit 220 based on the comparison at the comparator 422, which may include, by way of example and not limitation, sampling rate, digitization resolution, or time and duration of data acquisition period. For example, if the comparison at the comparator 422 indicates a decreased physical activity level indicating a likelihood of pain onset or worsening pain, the operating mode control 242 may control the second sensor circuit 220 to acquire data at a higher sampling rate or a higher digitization resolution, or with a longer data acquisition time period. This may help preserve the information of patient response to pain, and may improve pain assessment accuracy at the pain analyzer circuit 230. In an example, the second sensor circuit 220 may remain active acquiring data, or remain in high sampling rate or high resolution mode until the physical activity level stabilizes or exceeds a threshold indicating a pain relief or improvement. If the comparison at the comparator 422 indicates a high physical activity level, then the operating mode control 242 may reduce the sampling rate or the digitization resolution for the second sensor circuit 220, or control the second sensor circuit 220 to acquire data during a shorter data acquisition period. The operating mode control 242 may additionally or alternatively adjust data pre-processing of the data acquired by the second sensor circuit 220 based on the physical activity level, such as adjusting one or more parameters of signal filters including cutoff frequencies of a passband.

Operating mode of the second sensor as controlled by the physical activity level or other functional signals such as gait, balance, posture, range-of-motion, or sleep state may offer several benefits. Power and computing resources may be conserved by reducing the total activation time of second sensor, such as when the physical activity or other functional signals indicating a low likelihood of pain. The device power and computing resources may be reserved for sensor data collection and analysis in case of an elevated likelihood of pain such as indicated by reduced activity level. This may improve accuracy of pain quantification at the pain analyzer circuit 230, while reduce the overall operational cost of a pain management system such as an ambulatory pain monitor.

In some examples, the operating mode control 242 may determine operating modes associated with different sensors further based on sensor sensitivity to physical activity. The second sensor circuit 220 may acquire data from the different sensors according to their respectively determined operating modes. For example, some sensors, such as heart sound sensor, are sensitive to physical activity and may be susceptible to motion artifacts and other interferences during high activity periods, and thus become less reliable for use in pain quantification. The second sensor circuit 220 may withhold data acquisition from these sensors when a high activity level is detected at the first sensor circuit 420. On the other hand, certain sensors, such as EMG sensor, may not require a high sampling rate during periods of low activity (e.g., during sleep), while some other sensors, such as PPG or galvanic skin response (GSR) sensor, are not sensitive to changes in physical activity level. The second sensor circuit 220, in response to a low physical activity detected at the first sensor circuit 420, may withhold data acquisition or set a lower data acquisition rate for the EMG sensor, and set a high sampling rate for the PPG sensor or the GSR sensor.

The data sensed at the second sensor circuit 220 according to the determined operating mode may be used to assess pain at the pain analyzer circuit 230. In some examples, the extracted feature from the feature extractor circuit 421, such as features of posture, gait, physical activity, balance, or range-of-motion, may also be used to assess pain and generate a pain score at the pain analyzer circuit 230.

Figure 5:
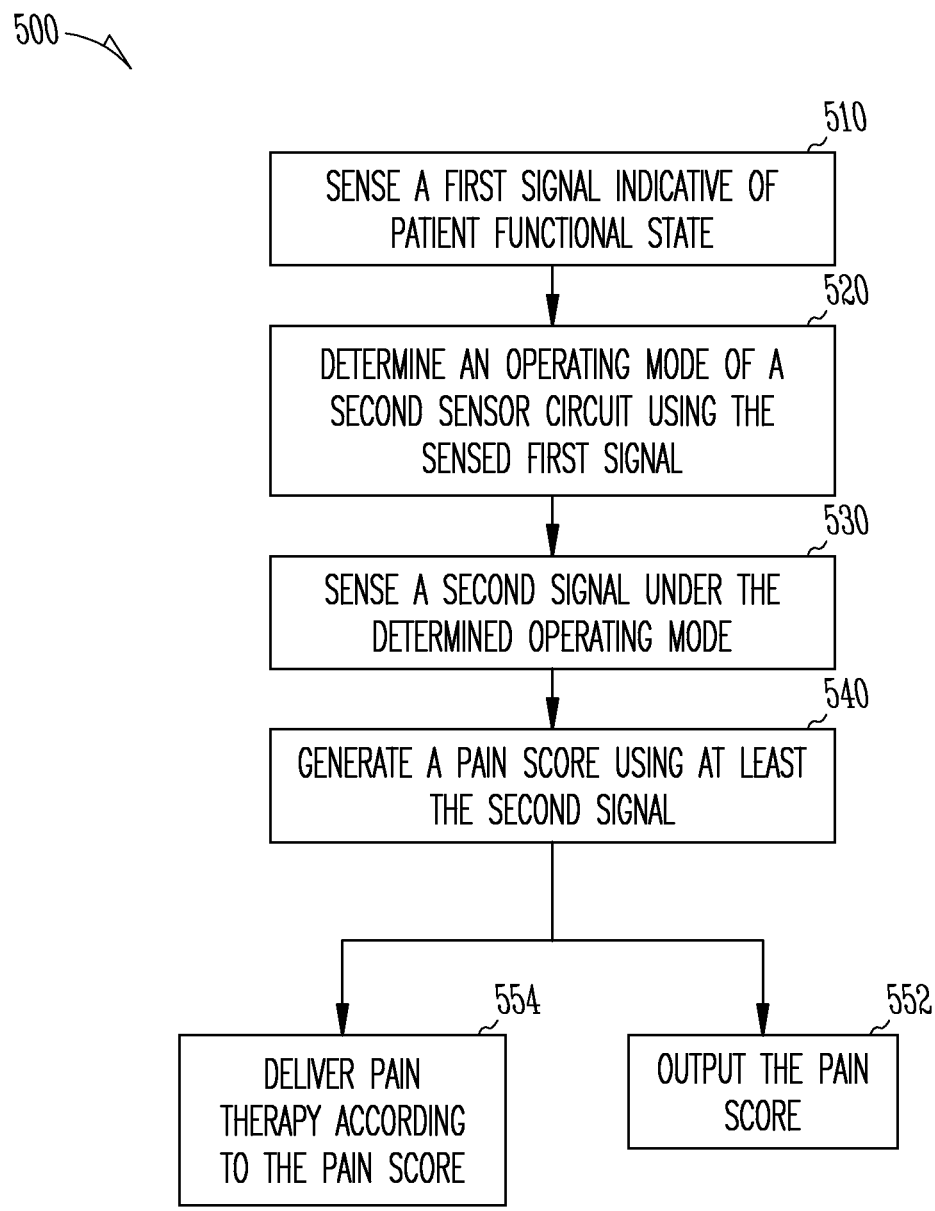
FIG. 5 illustrates, by way of example and not limitation, a method for managing pain of a patient.

FIG. 5 illustrates, by way of example and not limitation, a method 500 for managing pain of a patient. The method 500 may be implemented in a medical system, such as the pain management system 200 or 300. In an example, at least a portion of the method 500 may be executed by a neuromodulator device (IND) such as the implantable neuromodulator 310. In an example, at least a portion of the method 500 may be executed by an external programmer or remote server-based patient management system, such as the external system 320 that are communicatively coupled to the IND. The method 500 may be used to provide neuromodulation therapy to treat chronic pain or other disorders.

The method 500 begins at step 510, where a first signal indicative of patient functional state may be sensed from the patient. The functional state signal may include a motor activity signal. By way of example and not limitation, motor activity signal may include patient posture, gait, balance, range-of-motion, or physical activity signals, among others. In some examples, the functional state signal may include a sleep state signal that contains information about sleep disturbance. Examples of the sleep state signals may include pain indicators during sleep, such as frequency or duration of sleep position switch, sleep incline, or other indicators of sleep quality or change of sleep pattern. Chronic pain patients may present with poor or unbalanced posture, abnormal gait pattern, restrained range-of-motion, or decreased intensity or duration of physical activities. Pain may also cause frequent sleep disturbance and poor sleep quality. Monitoring patient motor control or sleep disturbance may provide an objective assessment of pain, and may be used to improve pain therapy efficacy. The functional signals may be sensed using electrodes or ambulatory sensors, such as one or more motion sensors 411-415 associated with patient in different manners, as illustrated in FIG. 4.

At 520, an operating mode of a second sensor circuit may be determined using the received first signal. The second sensor circuit, such as that illustrated in FIGS. 2 and 4, may be configured to sense a second signal different from the first signal sensed at 510 under a specified operating mode. The operating mode may include an activation or deactivation of sensor data acquisition by the second sensor circuit, or data sampling rate that the second sensor circuit uses for sampling the second signal. The operating mode may be determined using the control circuit 240 as illustrated in FIG. 2. The first signal sensed at 510 may be compared to a specific criterion, such as a threshold or a value range, to determine whether to activate the data acquisition, time of data acquisition, or sampling rate of data acquisition of the second signal based on the comparison. Using the first sensor signal to trigger activation and set operating mode of the second sensor may offer several benefits in pain management, particularly in ambulatory pain monitor and quantification. It may reduce power consumption and optimize device memory usage. The functional state as indicated by the first sensed signal may indicate a precursor of pain episode, and activation of data acquisition and analysis of the second signal may generate a reliable confirmation of pain episode or worsening of pain. Additionally, the functional signal may be used to prescreen the second sensor such as to determine proper time for data acquisition to avoid interferences or noise and thus allowing for a higher quality data for use in pain assessment.

In an example, the operating mode of the second senor circuit may be determined using one or more functional signal features of the first signal, such as extracted by the feature extractor circuit 421. Examples of the functional signal features may include physical activity features such as activity intensity, activity duration, or a transition time between different types of activities; body position features during sitting, standing, or walking; motor control and kinematic features such as lumbar forward flexion, shoulder flexion, elbow flexion, rotation of arm and elbow joint, trunk-pelvis rotation, or a rate or a pattern of change in motion with respect to time or with respect to angular velocity; gait features such as time to peak velocity, step length, stride length, stride width, swing time, single limb support time, double limb stance, gait autonomy, cadence; or sleep state features such as sleep incline, sleep sidedness, frequency of sleep position switch, or other sleep quality or sleep disturbance metrics, among other signal features.

The extracted functional signal feature may be measured and trended over time. In some examples, the functional signal features may be measured during a specified time period of daytime or nighttime, or in a specific context such as when the patient is asleep. The functional signal feature trend may be compared to one or more thresholds or one or more value ranges to determine patient functional state. The operating mode of the second sensor circuit may be determined based on the patient functional state. In some examples, a physical activity pattern may be detected, such as via the pattern detector 423, using measurements of the extracted feature over time. The detected physical activity pattern may be compared to a physical activity template representing a physical activity pattern under a known, controlled condition, such as a baseline pain-free condition. The operating mode of the second sensor circuit may be determined based on the comparison between the detected physical activity pattern and the physical activity template.

At 530, a second signal different from the first signal may be sensed, such as via the second sensor circuit 220, under the operating mode as determined at 520. The second signal may include cardiac, pulmonary, neural, biochemical, or other physiological signals. Some of these signals may reveal characteristic signal properties in response to an onset, intensity, severity, duration, or patterns of pain. Examples of the second signal may include cardiac signals such as a heart rate signal, a pulse rate signal, a heart rate variability signal, electrocardiograph (ECG) or intracardiac electrogram, cardiovascular pressure signal, or heart sounds signal, among others. The second signal may additionally or alternatively include a galvanic skin response (GSR) signal, an electrodermal activity (EDA) signal, a skin temperature signal, an electromyogram (EMG) signal, an electroencephalogram (EEG) signal, a magnetoencephelogram (MEG) signal, a hemodynamic signal such as a blood flow signal, a blood pressure signal, a blood perfusion signal, a photoplethysmography (PPG) signal, or a saliva production signal indicating the change of amount of saliva production, among others.

In an example, the operating mode of the second sensor circuit may be determined at 520 using a physical activity signal. Physical activity level may indicate presence or severity of pain. Patient in pain are generally less active, such that periods of activity are generally shorter and the activity intensity is generally lower. Therefore, a low physical activity level (in activity intensity or duration) may indicate a pain episode or precursor of pain has likely occurred, and a high physical activity level may indicate that the patient is not likely experiencing pain. In some examples, the physical activity may be measured during a specified time period of daytime or nighttime, or in a specific context such as when the patient is asleep. For example, a high physical activity level during a period of nighttime or during sleep may indicate onset of pain or undesirable pain treatment.

If the physical activity indicates that a pain episode or precursor of pain has likely occurred, then at 530, the data acquisition of the second signal, such as a cardiac, pulmonary, muscular, or neurological signal, may be initiated. Additionally, a higher data acquisition rate may be used in response to the detection of the low physical activity level, including one or more of a higher sampling rate, a higher digitization resolution, or a longer data acquisition time period, among others. This may preserve the information of patient response to pain, and thus improve the accuracy of pain quantification.

However, if the physical activity indicates that the patient is not likely experiencing pain, then at 530, the data acquisition of the second signal may be withheld, or the sensor circuit for sensing the second signal may be at least temporarily deactivated. The operating mode corresponding to the high physical activity level may additionally or alternatively include a lower data acquisition rate, including one or more of a lower sampling rate, a lower digitization resolution, or a shorter data acquisition time period, among others. When the physical activity or other functional signals indicate a low likelihood of pain, by reducing the activation time or acquiring data at lower data rate may save power and computing resources. Power and computing resources may be reserved for sensor data collection and analysis in case of an elevated likelihood of pain such as indicated by reduced activity level.

In some examples, at 520, operating modes associated with different sensors may be determined further based on a sensor's sensitivity to physical activity. Some sensors, such as heart sound sensor, are more sensitive to physical activity and susceptible to motion artifacts and other interferences during high activity periods, and thus become less reliable for use in pain quantification. On the other hand, certain sensors, such as EMG sensor, may not require a high sampling rate during periods of low activity (e.g., during sleep), while some other sensors, such as PPG or galvanic skin response (GSR) sensor, are not sensitive to changes in physical activity level. At 530, sensor data may be acquired from different sensors according to their respectively determined operating modes. For example, when a high activity level is detected, the sensors that are more susceptible to interferences and noises are at least temporarily deactivated, the data acquisition from these sensors can be withheld. When a low physical activity detected, data acquisition of EMG may be withheld or set a lower data acquisition rate, and the PPG or the GSR signal may be acquired at a higher data acquisition rate.

At 540, a pain score may be generated using at least the second signal sensed under the determined operating mode, such as via the pain score generator 232. The pain score may be generated using signal metrics generated from the second signal sensed under the determined operating mode. The signal metrics may include statistical parameters, morphological parameters, or timing information such as a time interval between a first characteristic point in one signal and a second characteristic point in another signal. In an example, a composite signal metric may be generated using a combination of a plurality of the signal metrics respectively weighted by weight factors. The combination can be linear or nonlinear. The composite signal metric may be categorized as one of a number of degrees of pain by comparing the composite signal metric to one or more threshold values or range values, and a corresponding pain score may be assigned based on the comparison. In another example, the signal metrics may be compared to their respective threshold values or range values and a corresponding signal metric-specific pain score may be determined. A composite pain score may be generated using a linear or nonlinear fusion of the signal metric-specific pain scores each weighted by their respective weight factors. In some examples, the pain score may be computed using a subset of the signal metrics selected based on their temporal profile of pain response. Signal metrics with quick pain response (or a shorter transient state of response) may be selected to compute the pain score during a pain episode. Signal metrics with slow or delayed pain response (or a longer transient state of response before reaching a steady state) may be used to compute the pain score after an extended period following the onset of pain such as to allow the signal metrics to reach steady state of response. In some examples, patient demographic information such as patient age or gender may be used in computing the pain score. A higher pain threshold for the composite signal metric may be selected for male patients than for female patients. Additionally or alternatively, the respective weight factors may be determined based on patient demographic information. The weight factors for the signal metrics may be tuned to a lower value than the weight factors for the same signal metric in a female patient.

At 552, the pain score may be output to a user or to a process, such as via the output circuit as illustrated in FIG. 2. The pain score, including the composite pain score and optionally together with metric-specific pain scores, may be displayed on a display screen. Other information such as the functional signals and the signal metrics extracted from the functional signals may also be output for display or for further processing. In some examples, alerts, alarms, emergency calls, or other forms of warnings may be generated to signal the system user about occurrence of a pain episode or aggravation of pain as indicated by the pain score.

The method 500 may include, at 554, an additional step of delivering a pain therapy to the patient according to the pain score. The pain therapy may include electrostimulation therapy, such as spinal cord stimulation (SCS) via electrodes electrically coupled to the electrostimulator. The SCS may be in a form of stimulation pulses that are characterized by pulse amplitude, pulse width, stimulation frequency, duration, on-off cycle, waveform, among other stimulation parameters. Other electrostimulation therapy, such as one or a combination of DBS, FES, VNS, TENS, or PNS at various locations, may be delivered for pain management. The pain therapy may additionally or alternatively include a drug therapy such as delivered by using an intrathecal drug delivery pump.

In various examples, the pain therapy (such as in the form of electrostimulation or drug therapy) may be delivered in a closed-loop fashion. Therapy parameters, such as stimulation waveform parameters, stimulation electrode combination and fractionalization, drug dosage, may be adaptively adjusted based at least on the pain score. The pain-relief effect of the delivered pain therapy may be assessed based on the signal metrics such as the cardiovascular parameters, and the therapy may be adjusted to achieve desirable pain relief. The therapy adjustment may be executed continuously, periodically at specific time, duration, or frequency, or in a commanded mode upon receiving from a system user a command or confirmation of parameter adjustment. In an example, if the pain score exceeds the pain threshold (or falls within a specific range indicating an elevated pain), then the first electrostimulation may be delivered. Conversely, if the composite pain score falls below a respective threshold value (or falls within a specific range indicating no pain or mild pain), then a second pain therapy, such as second electrostimulation may be delivered. The first electrostimulation may differ from the second electrostimulation with respect to at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. In some examples, the responses of the signal metrics to pain therapy delivered at 544 may be used to gauge composite pain score computation such as by adjusting the weight factors. In an example, weight factors may be determined and adjusted via the weight generator 322 as illustrated in FIG. 3, to be proportional to signal metric's sensitivity to pain.

Figure 6:
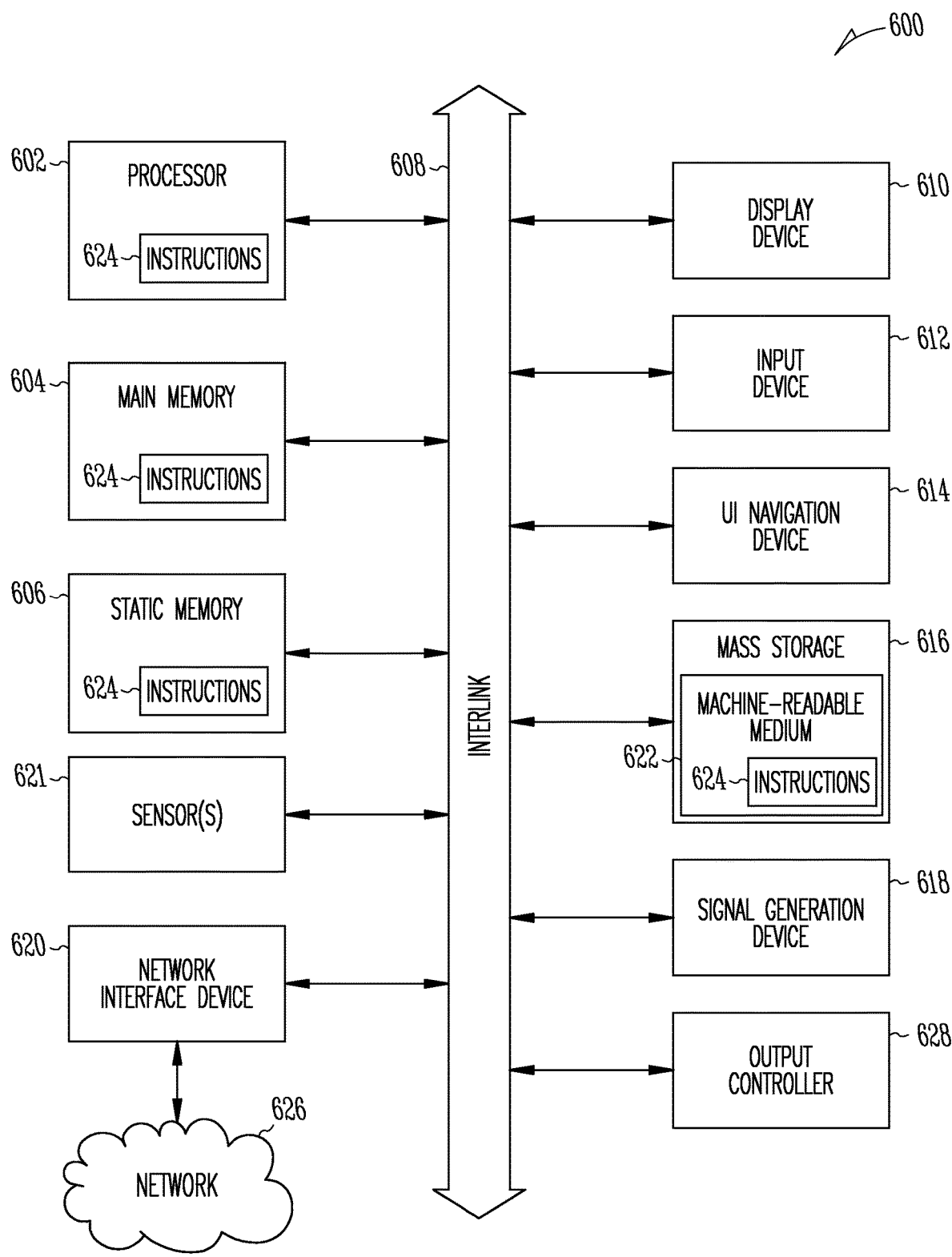
FIG. 6 illustrates, by way of example and not limitation, a block diagram of an example machine upon which any one or more of the techniques discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system comprising:
   a sensor circuit, comprising (i) a physiological sensor configured to sense a physiological signal from a patient, and (ii) a motion sensor configured to detect a physical activity pattern of the patient representing a change in physical activity over time; and a controller circuit configured to:
determine a baseline physical activity pattern at a baseline state of the patient;
control the physiological sensor to initiate sampling of the physiological signal based on a dissimilarity between the detected physical activity pattern and the baseline physical activity pattern; and
generate a control signal to initiate or adjust a neuromodulation therapy to the patient in response to the sampled physiological signal satisfying a condition.

2. The system of claim 1, wherein the physical activity pattern includes a decrease in activity level over time or missing of a scheduled activity at a predetermined time.

3. The system of claim 1, wherein the controller circuit is further configured to:
control the physiological sensor to adjust a sampling rate of the physiological signal based on the dissimilarity between the detected physical activity pattern and the baseline physical activity pattern; and
generate the control signal to initiate or adjust the neuromodulation therapy in response to the physiological signal sampled at the adjusted sampled rate satisfying the condition.

4. The system of claim 3, wherein the baseline physical activity pattern corresponds to a baseline state free of pain, and wherein the controller circuit is configured to:
determine a pain score using the sampled physiological signal; and
generate the control signal to initiate or adjust the neuromodulation therapy according to the generated pain score to alleviate pain.

5. The system of claim 3, wherein the controller circuit is configured to control the physiological sensor to increase the sampling rate for sampling the physiological signal when the determined dissimilarity exceeds a threshold.

6. The system of claim 5, wherein the baseline physical activity pattern includes a baseline rate of change in activity level during a specific time period of day, and the detected physical activity pattern includes a detected rate of change in activity level during the specific time period of day;
wherein the controller circuit is configured to control the physiological sensor to increase the sampling rate of the physiological signal when a difference between the detected rate of change and the baseline rate of change exceeds the threshold.

7. The system of claim 3, wherein the baseline physical activity pattern includes a scheduled activity at a predetermined time of day,
wherein the controller circuit is configured to control the physiological sensor to increase the sampling rate of the physiological signal when the determined dissimilarity indicates the scheduled activity is missing from the detected physical activity at the predetermined time of day.

8. A system comprising:
a sensor circuit coupled to a plurality of physiological sensors each having respective sensitivities to physical activity, the plurality of physiological sensors configured to sense respective physiological signals from a patient; and
a controller circuit configured to:
receive information about a physical activity level in the patient;
select, from the plurality of physiological sensors, at least one physiological sensor based on the received physical activity level, including to select a first physiological sensor to sense a first physiological signal under a first sensor operating mode when the received physical activity level is above a threshold, and to select a second physiological sensor different from the first physiological sensor to sense a second physiological signal under a second sensor operating mode when the received physical activity level is below the threshold; and
generate a control signal to initiate or adjust a neuromodulation therapy to the patient based on the physiological signal sensed by the selected at least one physiological sensor.

9. The system of claim 8, wherein the controller circuit is configured to, when the received physical activity level exceeds a first threshold:
identify the at least one physiological sensor that has a lower sensitivity than other of the plurality of physiological sensors; and
sampling the physiological signal via the identified at least one physiological sensor at an increased sampling rate.

10. The system of claim 9, wherein the identified at least one sensor with the lower sensitivity includes at least one of a photoplethysmography (PPG) sensor or a galvanic skin response (GSR) sensor.

11. The system of claim 8, wherein the controller circuit is configured to, when the received physical activity level is below a second threshold:
identify the at least one physiological sensor that has a higher sensitivity to physical activity than other of the plurality of physiological sensors; and
sampling the physiological signal via the identified at least one physiological sensor at an increased sampling rate.

12. The system of claim 11, wherein the identified at least one sensor with the higher sensitivity includes a heart sound sensor.

13. The system of claim 8, wherein the controller circuit is configured to, when the received physical activity level is below a second threshold:
identify the at least one physiological sensor including an electromyography (EMG) sensor; and
decrease a sampling rate for sampling an EMG signal sensed by the EMG sensor.

14. A method of operating a neuromodulation device to provide neuromodulation to a patient, the method comprising:
determining a baseline physical activity pattern at a baseline state of the patient;
detecting a physical activity pattern from a motion signal sensed from the patient, the physical activity pattern representing a change in physical activity over time;
via a physiological sensor, initiating sampling of a physiological signal based on a dissimilarity between the detected physical activity pattern and the baseline physical activity pattern; and
via a control circuit, initiating or adjusting a neuromodulation therapy in response to the sampled physiological signal satisfying a condition.

15. The method of claim 14, comprising:
adjusting a sampling rate of the physiological signal based on the dissimilarity between the detected physical activity pattern and the baseline physical activity pattern; and initiating or adjusting the neuromodulation therapy in response to the physiological signal sampled at the adjusted sampled rate satisfying the condition.

16. The method of claim 15, wherein the baseline physical activity pattern includes a baseline rate of change in activity level during a specific time period of day, and the detected physical activity pattern includes a detected rate of change in activity level during the specific time period of day;

wherein adjusting the sampling rate of the physiological signal includes increasing the sampling rate of the physiological signal when a difference between the detected rate of change and the baseline rate of change exceeds a threshold.

17. The method of claim 15, wherein the baseline physical activity pattern includes a scheduled activity at a predetermined time of day, wherein adjusting the sampling rate of the physiological signal includes increasing the sampling rate of the physiological signal when the determined dissimilarity indicates the scheduled activity is missing from the detected physical activity at the predetermined time of day.

18. The method of claim 14, further comprising:
detecting a physical activity level from the motion signal; and
identifying, from a plurality of physiological sensors having respective sensitivities to physical activity, at least one physiological sensor based on the detected physical activity level;
wherein initiating or adjusting the neuromodulation therapy is based on the physiological signal sensed by the identified at least one physiological sensor.

19. The method of claim 18, comprising:
when the detected physical activity level exceeds a first threshold identifying the least one physiological sensor that has a lower sensitivity than other of the plurality of physiological sensors; and
sampling the physiological signal via the identified at least one physiological sensor at an increased sampling rate.

20. The method of claim 18, comprising:
when the detected physical activity level is below a second threshold, identifying the at least one physiological sensor that has a higher sensitivity to physical activity than other of the plurality of physiological sensors; and
sampling the physiological signal via the identified at least one physiological sensor at an increased sampling rate.

* * * * *